US011666409B2

(12) United States Patent
Amanatullah et al.

(10) Patent No.: US 11,666,409 B2
(45) Date of Patent: Jun. 6, 2023

(54) METHOD FOR MONITORING OBJECT FLOW WITHIN A SURGICAL SPACE DURING A SURGERY

(71) Applicant: The Board of Trustees of the Leland Stanford Junior University, Stanford, CA (US)

(72) Inventors: Derek F. Amanatullah, Stanford, CA (US); Rahim Nazerali, Stanford, CA (US); David Y. Zhao, Stanford, CA (US); Albert Haque, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 98 days.

(21) Appl. No.: 16/932,607

(22) Filed: Jul. 17, 2020

(65) Prior Publication Data

US 2021/0000564 A1  Jan. 7, 2021

Related U.S. Application Data

(63) Continuation-in-part of application No. 16/533,632, filed on Aug. 6, 2019.

(60) Provisional application No. 62/875,283, filed on Jul. 17, 2019, provisional application No. 62/715,119, filed on Aug. 6, 2018, provisional application No. 62/715,132, filed on Aug. 6, 2018.

(51) Int. Cl.
*A61B 90/00* (2016.01)
*A61B 50/36* (2016.01)

(52) U.S. Cl.
CPC ............ *A61B 90/08* (2016.02); *A61B 50/362* (2016.02); *A61B 90/361* (2016.02); *A61B 90/37* (2016.02); *A61B 2090/0804* (2016.02); *A61B 2090/0807* (2016.02); *A61B 2562/0233* (2013.01)

(58) Field of Classification Search
CPC ....... A61B 90/08; A61B 50/36; A61B 50/362; A61B 90/36; A61B 90/361; A61B 90/3612; A61B 90/3614; A61B 90/3616; A61B 90/3618; A61B 90/363; A61B 90/37; A61B 2090/0803; A61B 2090/0804; A61B 2090/0807; A61B 2562/0233
USPC ........................................................... 606/1
See application file for complete search history.

(56) References Cited

U.S. PATENT DOCUMENTS

2015/0305735 A1* 10/2015 Gorek .................... A61B 50/20
606/147

* cited by examiner

*Primary Examiner* — Aaron F Roane
(74) *Attorney, Agent, or Firm* — Run8 Patent Group, LLC; Peter Miller

(57) ABSTRACT

One variation of a method for monitoring needle consumption in a surgical space during a surgery includes: accessing a sequence of images captured by a camera facing an inventory field within the surgical space; scanning the sequence of images for needle packages and needles; in response to detecting entry of a needle package into the surgical space in a first image, logging entry of the needle package, labeled as sterile, into the inventory field at a first time and incrementing a sterile packaged needle counter for the needle package according to a first quantity of sterile needles associated with a type of the needle package; and, in response to detecting removal of a first needle from the inventory field in a second image, incrementing a deployed needle counter at a second time succeeding the first time and decrementing the sterile packaged needle counter.

20 Claims, 8 Drawing Sheets

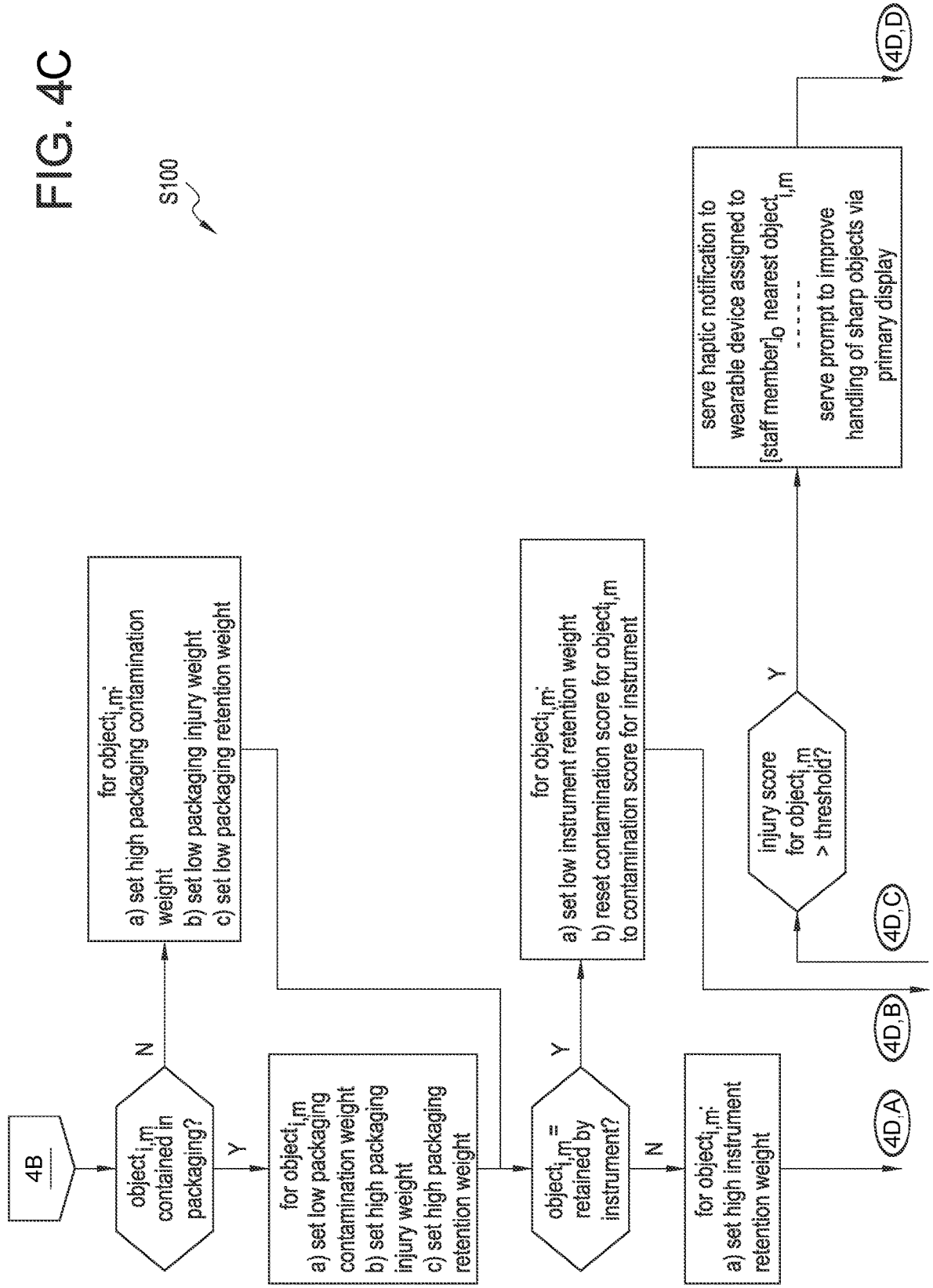

METHOD FOR MONITORING OBJECT FLOW WITHIN A SURGICAL SPACE DURING A SURGERY

CROSS-REFERENCE TO RELATED APPLICATIONS

This application claims the benefit of U.S. Provisional Patent Application No. 62/875,283, filed on 17 Jul. 2019, which is incorporated in its entirety by this reference.

This application is a continuation-in-part application of U.S. patent application Ser. No. 16/533,632, filed on 6 Aug. 2019, which claims the benefit of U.S. Provisional Application No. 62/715,119, filed on 6 Aug. 2018, and U.S. Provisional Application No. 62/715,132, filed on 6 Aug. 2018, each of which is incorporated in its entirety by this reference.

TECHNICAL FIELD

This invention relates generally to the field of virtual surgical tools and more specifically to a new and useful method for monitoring object flow within a surgical space during a surgery in the field of virtual surgical tools.

BRIEF DESCRIPTION OF THE FIGURES

FIGS. 4A, 4B, 4C and 4D are a flowchart representation of one variation of the method.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
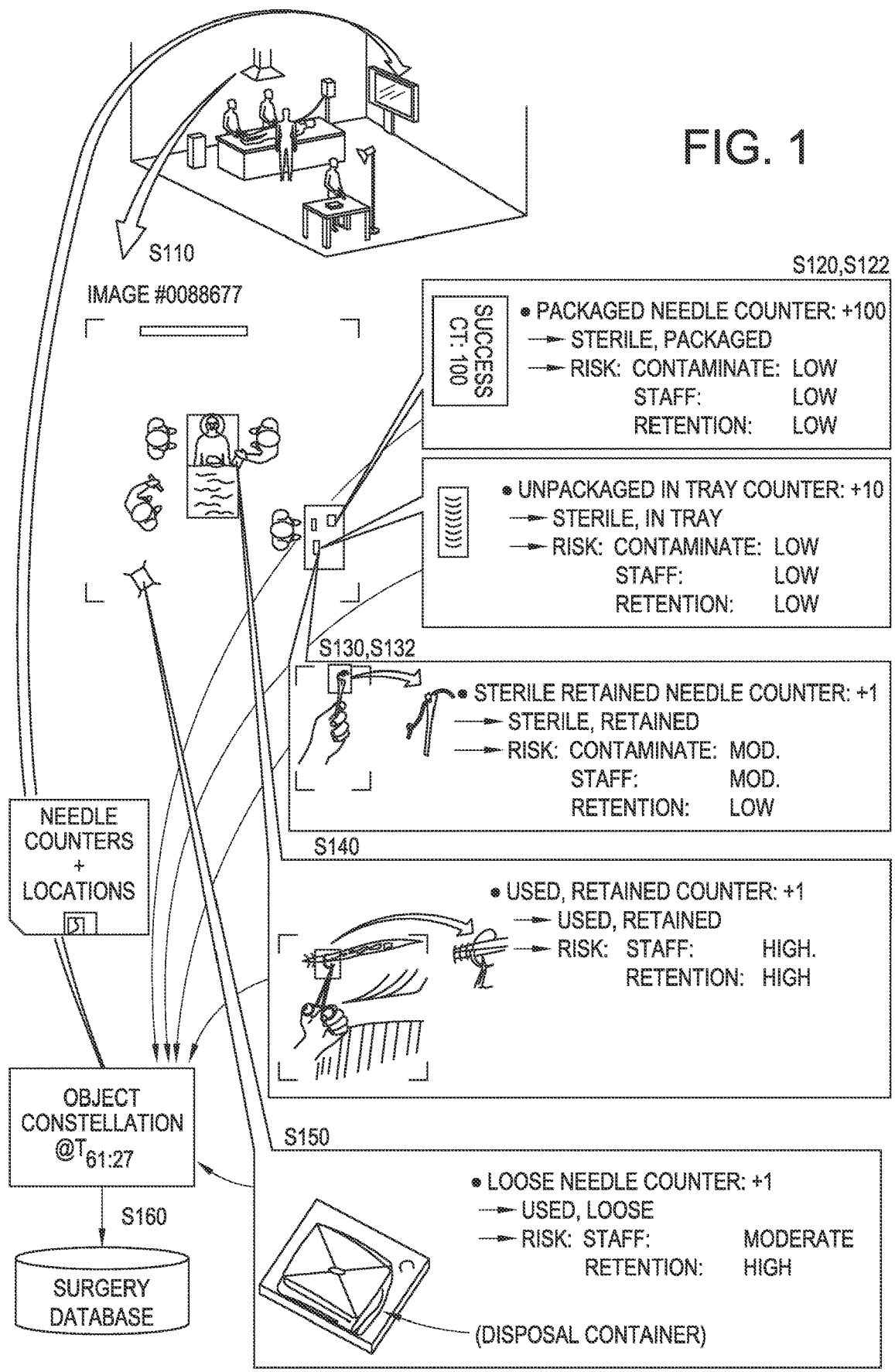
FIG. 1 is a flowchart representation of a method.

As shown in FIG. 1, a method S100 for monitoring object flow within a surgical space during a surgery includes: accessing a sequence of images of a surgical space captured by a set of optical sensors arranged in the surgical space in Block Silo; and, in response to detecting a needle package at a first location in a first image, in the sequence of images, captured at a first time, logging a first needle in a sterile packaged condition at the first location at the first time in Block S120. The method S100 also includes, in response to detecting a needle driver at a second location in a second image, in the sequence of images, captured at a second time succeeding the first time: scanning a second region of the second image depicting a distal end of the needle driver for features representative of the first needle in Block S130; and, in response to detecting features representative of the first needle in the second region of the second image, logging the first needle in a sterile retained condition proximal the second location at the second time in Block S130. The method S100 further includes, in response to detecting the needle driver at a third location in a third image, in the sequence of images, captured at a third time succeeding the second time: scanning a third region of the third image depicting the distal end of the needle driver for features representative of a patient in Block S140; and, in response to detecting features representative of the patient in the third region of the third image, logging the first needle in a used retained condition proximal the third location at the third time in Block S140. The method S100 also includes, in response to detecting the needle driver at a fourth location in a fourth image, in the sequence of images, captured at a fourth time succeeding the third time: scanning a fourth region of the fourth image depicting the distal end of the needle driver for features representative of a needle disposal container in Block S150; and, in response to detecting features representative of the needle disposal container in the fourth region of the fourth image, logging the first needle in a disposed condition proximal the fourth location at the fourth time in Block S150. The method S100 further includes aggregating logs of locations and conditions of the first needle into a first path of the first needle during the surgery in Block S160.

One variation of the method S100 includes: accessing a sequence of images of a surgical space captured by a set of optical sensors arranged in the surgical space in Block Silo; and, in response to detecting a needle package in a first image, in the sequence of images, of an inventory field in the surgical space, logging entry of a first set of needles in a sterile packaged condition at the inventory field at a first time in Block S120. This variation of the method S100 also includes, for each needle in the first set of needles: in response to detecting a needle driver in a second image, in the sequence of images, of the inventory field, scanning the second image for a needle proximal a distal end of the needle driver in Block S130 and, in response to detecting the needle proximal the distal end of the needle driver in the second image, logging the needle in a sterile retained condition in the inventory field at a second time in Block S130; in response to detecting the needle driver in a third image, in the sequence of images, of an operating field in the surgical space, scanning the third image for features representative of a patient proximal the distal end of the needle driver in Block S140 and, in response to detecting features representative of the patient proximal the distal end of the needle driver in the third image, logging the needle in a used retained condition proximal the patient at a third time in Block S140; aggregating logs of locations and conditions of the needle into a path of the needle during the surgery in Block S160; and storing the path of the needle with a set of needle paths occurring during the surgery in Block S160. This variation of the method S100 further includes characterizing performance during the surgery based on the set of needle paths in Block S170.

Figure 2A:
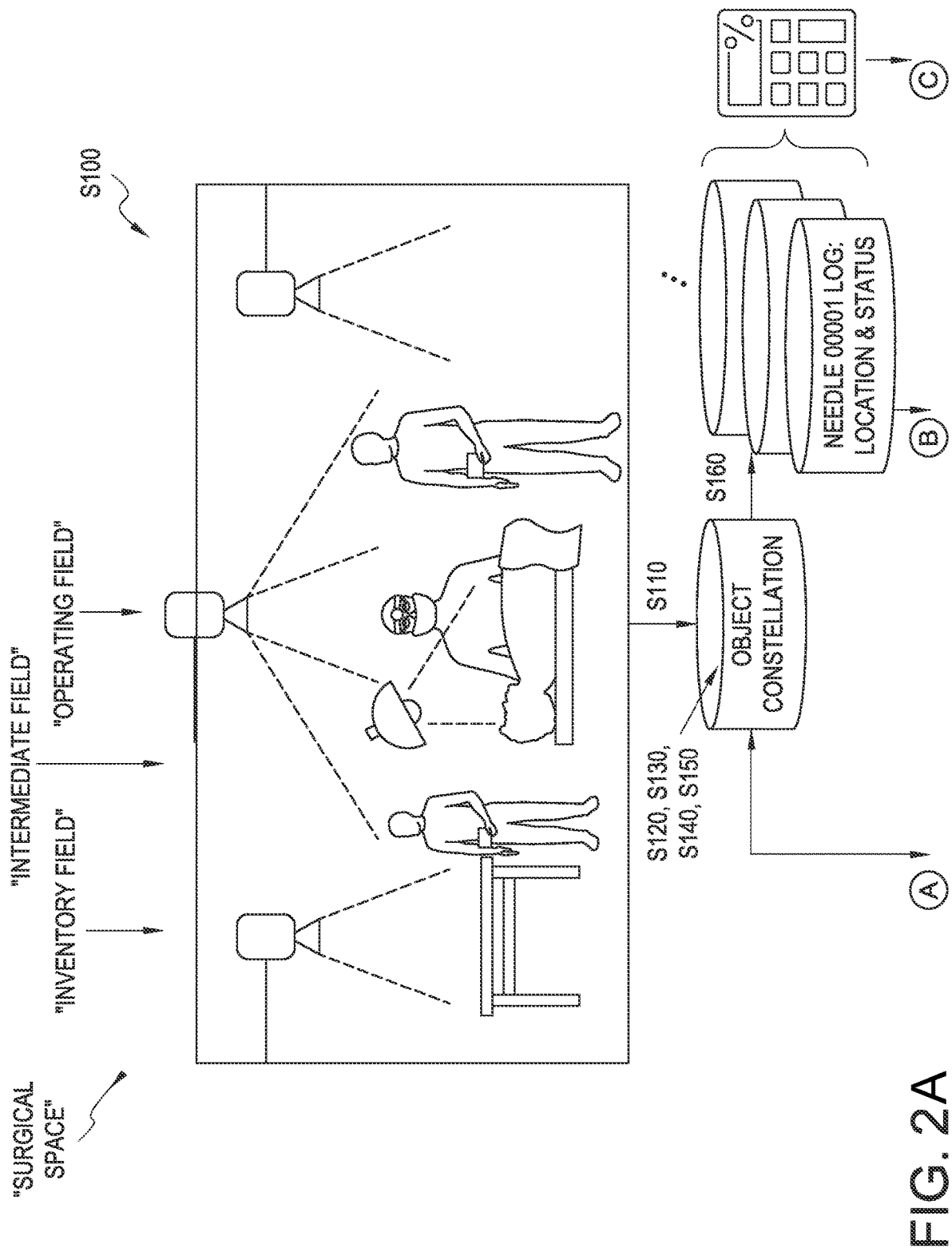
FIGS. 2A and 2B is a flowchart representation of one variation of the method.
Figure 2B:
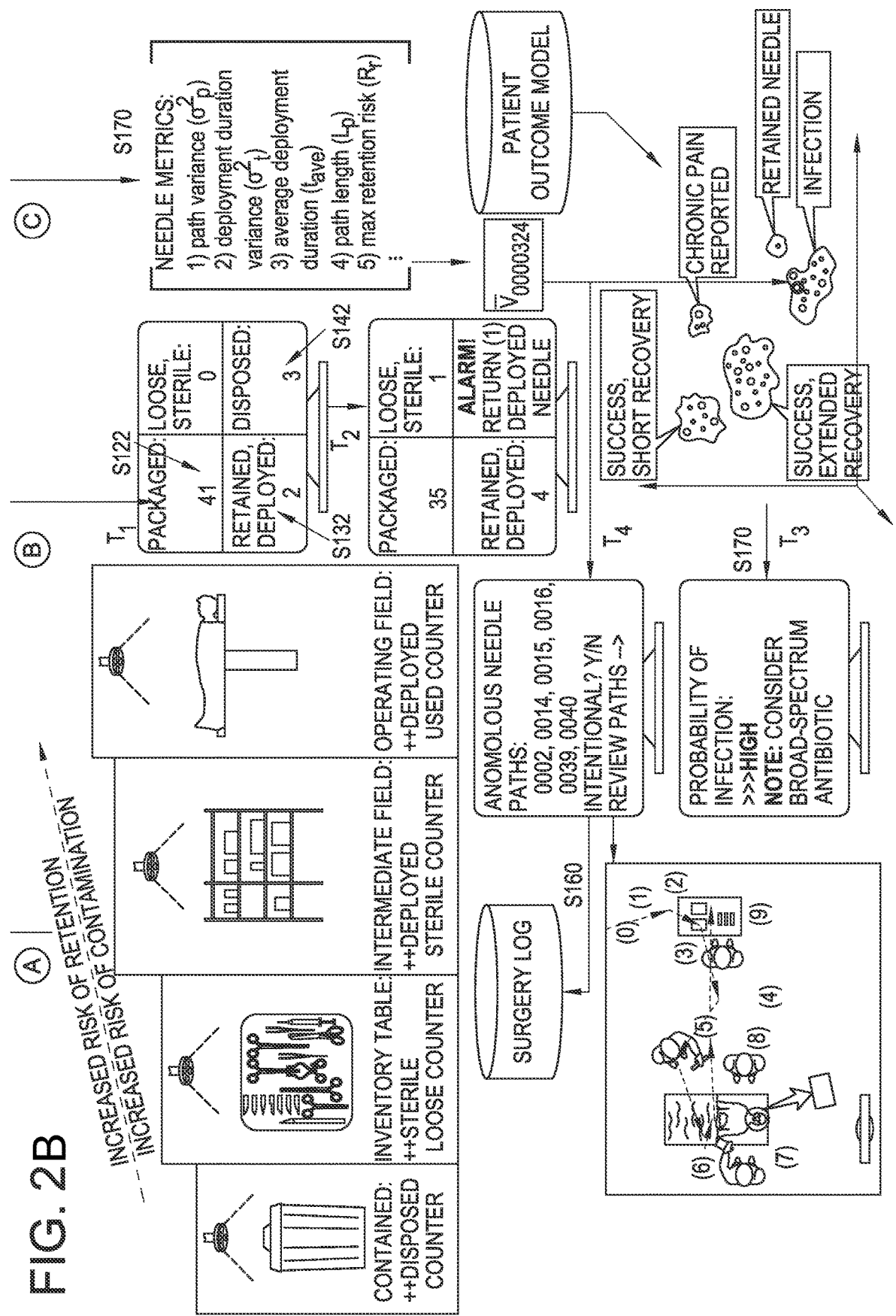

Another variation of the method S100 shown in FIG. 2 includes: accessing a sequence of images captured by a set of optical sensors facing an inventory field within the surgical space in Block S110; and scanning the sequence of images for features representative of needle packages and needles in Block S120. This variation of the method S100 also includes, in response to detecting entry of a needle package into the surgical space in a first image, in the sequence of images: logging entry of the needle package, labeled as sterile, into the inventory field at a first time in Block S120; and incrementing a sterile packaged needle counter for the needle package according to a first quantity of sterile needles associated with a type of the needle package in Block S122. This variation of the method S100 further includes, in response to detecting removal of a first needle from the inventory field in a second image, in the sequence of images: incrementing a deployed needle counter at a second time succeeding the first time in Block S132; and decrementing the sterile packaged needle counter in Block S132. This variation of the method S100 also includes, in response to detecting return of the first needle to the inventory field in a third image, in the sequence of images: labeling the first needle in the third image as used at a third time succeeding the second time in Block S140; and decrementing the deployed needle counter in the log in Block S142.

2. Applications

Generally, Blocks of the method S100 can be executed by a computer system (e.g., a local computing device, a computer network, a remote server): to detect and track surgical needles for suturing (hereinafter "needles") in a live feed of images of a surgical space during a surgery; to interpret sterility and use conditions of these needles based on their locations and interactions with other objects in the surgical space; and to assemble these data into timeseries path and condition data for individual needles moving through the surgical space during the surgery.

The computer system can then derive inter-operative insights based on these timeseries path and condition data for individual needles and then present these inter-operative insights to surgical staff in (near) real-time during the surgery, such as to enable these surgical staff to: preempt needle shortages; retrieve lost needles; verify sterility of needles before insertion into a patient; detect and handle needle sticks on surgical staff members; distinguish broken and intact needles; and/or audit and address processes in the surgical space in real-time when contamination, staff, or retention risk for needles in the surgical space increase; etc. The computer system can also derive objective post-operative insights for the surgery based on these timeseries needle path, needle type, and condition data, such as: efficiency of the surgery; complexity of the surgery; performance of the surgical staff; low-efficiency needle-related operations that may be modified to increase surgery efficiency; and/or needle-related operations that may be modified to reduce contamination or staff injury risk. More specifically, the computer system can leverage inter-operative needle consumption data captured during a surgery to derive objective insights and documentation of efficiency, complexity, and/or risk of the surgery.

Furthermore, the computer system can predict patient outcome following the surgery based on these timeseries needle path and condition data, such as: patient recovery time as a function of quantity of needles consumed during the surgery; and/or risk of infection for the patient based on contamination risk of needles consumed over the duration of the surgery.

Therefore, the computer system can execute Blocks of the method S100 to: implement computer vision techniques to detect and track locations of individual needles and other instruments and objects within a surgical space throughout a surgery; leverage ontologies or contextual awareness of relationships between needles and surgical staff, a patient, a needle driver, and other instruments and objects within the surgical space to track sterility and real-time use conditions of individual needles; monitor contamination, staff, and/or retention risk for individual needles; and derive and present real-time inter-operative guidance for tracking needles, increasing needle-related efficiencies, and reducing needle-related risks to surgical staff during the surgery. The computer system can also execute Blocks of the method S100 to quantify the surgery, to predict and address an outcome of the surgery, and surface opportunities for increasing efficiency and reducing risk related to needle consumption within surgeries based on timeseries needle data from one or many surgeries.

The method S100 is described herein as executed by the computer system to monitor and characterize needle consumption within a surgical space. However, any other local or remote computer system can implement similar methods and techniques to monitor and characterize consumption of surgical sponges, surgical towels, surgical instruments, or an object of any other type within a surgical space. Furthermore, the computer system or other system can execute similar methods and techniques to detect, track, characterize states, and interpret various risk characteristics, and maintain real-time counters of other surgical objects, such as: surgical gauzes; surgical retractors; forceps; syringes; scissors; surgical blades; etc. The computer system can also predict surgical outcomes for patients based on states, consumption, paths, etc. of these surgical objects, such as described below.

3. Images

Block S110 of the method S100 recites accessing a sequence of images of a surgical space captured by an optical sensor arranged in the surgical space. Generally, in Block S110, the computer system can access a stream of images captured by a set of cameras arranged in or facing the surgical space. For example, the set of cameras can include a color (e.g., RGB) camera, a 3D stereoscopic color camera, an infrared camera, a multi-spectral imager, and/or a 2D or 3D depth sensor. The set of cameras can also return 2D or 3D color images, depth maps, or point clouds (e.g., 3D color point clouds) to the computer system for processing on regular intervals, such as 30 Hz or 60 Hz.

In one implementation, a camera is fixed to a stand overhead an inventory table—offset from an operating table—in the surgical space such that images captured by the camera depict packaged and unpackaged needles in inventory in the surgical space. Alternatively, the camera can be mounted directly over or facing the operating table such that images captured by the camera depict needles handled by a surgeon, inserted into a patient, and withdrawn from the patient.

3.1 Multiple Cameras

Alternatively, multiple cameras can be arranged in the surgical space with overlapping fields of view. For example: a first camera can be arranged over an inventory field in the surgical space and capture images of the inventory table; a second camera can be arranged over an operating field in the surgical space and can capture images of the operating table; and a third camera can be arranged over an intermediate field between the inventory field and the operating field and can capture images of surgical staff and objects (e.g., needles and needle drivers) moving between the inventory field and the operating field. In this example, the third camera can define a field of view that overlaps the fields of view of the first and second cameras, such as 30% area overlaps at a plane intersecting the floor of the surgical space. In this implementation, the computer system can implement methods and techniques described below to individually process (approximately) concurrent images output by these cameras and track objects moving between the inventory and operating fields during the surgery based on known positions of these cameras and features—representative of these objects—detected in images output by these cameras. Alternatively, the computer system can stitch (approximately)

concurrent images output by these cameras into composite images spanning the preparation, intermediate, and operating fields based on known positions of these cameras and then implement methods and techniques described below to detect objects (e.g., needles, needle drivers) in these composite images and to thus track these objects moving within the surgical space.

3.2 Imaging Resolution as Function of Field Type with Multiple Cameras

In a similar implementation, the computer system: accesses a first sequence of images from a first cluster of optical sensors facing and configured to image the inventory field; fuses images from the first cluster of optical sensors (or otherwise processes these images) to form a representation of the inventory field at a first (high) optical resolution; and implements methods and techniques described below to detect and track needles, needle packages, and/or needle drivers within this representation of the inventory field. Similarly, the computer system can: access a second sequence of images from a second cluster of optical sensors facing and configured to image the operating field; fuse images from the second cluster of optical sensors (or otherwise process these images) to form a representation of the operating field at a second (high) optical resolution; and implement methods and techniques described below to detect and track needles, needle packages, needle drivers, surgical staff, and/or the patient within this representation of the operating field. Furthermore, the computer system can: access a third sequence of images from a third cluster of optical sensors facing and configured to image an intermediate field between the inventory and operating fields; fuse images from the third cluster of optical sensors (or otherwise process these images) to form a representation of the operating field at a third (low) optical resolution; and implement methods and techniques described below to detect and track needle drivers and/or surgical staff within this representation of the operating field.

For example, the first cluster of optical sensors can include a first quantity of (e.g., three) optical sensors, arranged in a first density over the span of the inventory table, arranged within a first (short) distance (e.g., 80 centimeters) of the inventory table, and/or individually characterized by high optical resolution (e.g., 50 megapixels) in order to support capture of optical data of sufficient resolution to enable the computer system to detect and track individual suture needles moving within the inventory field. In this example, the second cluster of optical sensors can similarly include a second (large) quantity of (e.g., 10) optical sensors, arranged in a second density (e.g., greater than the first density) over the span of the operating table, and/or individually characterized by high optical resolution (e.g., 100 megapixels) in order to support capture of optical data of sufficient resolution to enable the computer system to detect and track individual suture needles moving within and around the patient. Furthermore, in this example, the third cluster of optical sensors can include a third (smaller) quantity of (e.g., 3) optical sensors, arranged in a third density (e.g., less than the first and second densities) over the span of the intermediate field, and/or individually characterized by lower optical resolution (e.g., 20 megapixels) in order to support capture of optical data of sufficient resolution to enable the computer system to detect and track needle drivers moving between the inventory and operating fields (but not necessarily track individual suture needles retained by these needle drivers moving within the intermediate field).

Figure 3:
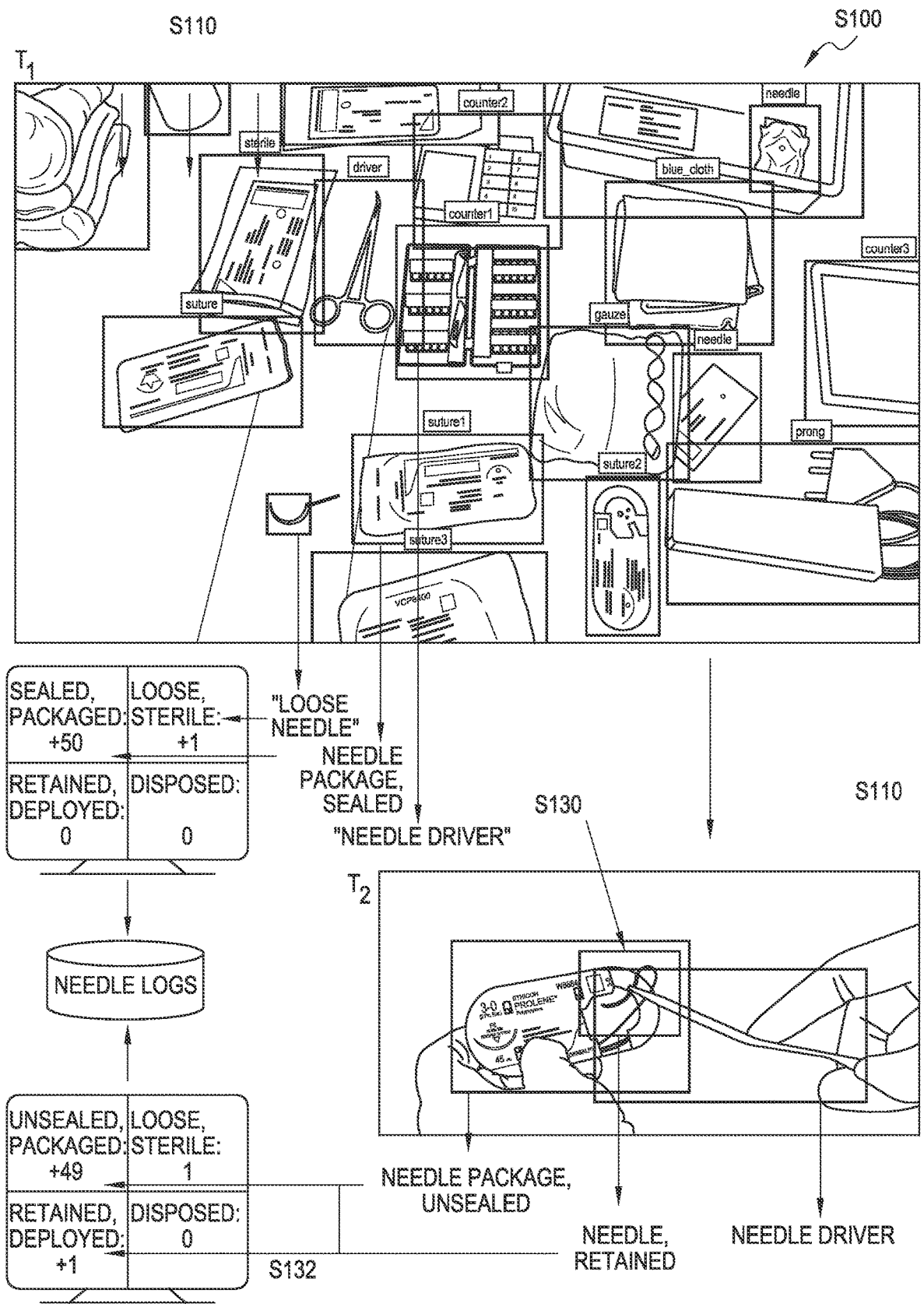
FIG. 3 is a flowchart representation of one variation of the method.

Therefore, in this implementation, the computer system can: track needles, removed from a needle package, in the inventory field based on locations of features representative of needles detected in a first sequence of images captured by the first cluster of optical sensors; track needles, manipulated near the patient, in the operating field based on locations of features representative of needles detected near distal ends of needle drivers detected in a second sequence of images captured by the second cluster of optical sensors, as shown in FIG. 3; and track needles moving between the inventory field and the operating field based on locations of features representative of needle drivers (and not necessary individual needles) detected in a third sequence of images captured by the third cluster of optical sensors, as shown in FIGS. 1 and 2.

However, the computer system can access and process images of any other type or resolution and from any other quantity of optical sensors according to Blocks of the method S100 in order to detect, track, and characterize individual needles and other objects present within the surgical space.

4. Object Detection and Tracking in Surgical Space

As shown in FIG. 3, the computer system can then implement computer vision techniques to detect locations and states of needles depicted in an image captured by the camera(s).

In one implementation, upon receipt of a next image from the camera, the computer system scans the image for features representative of needle packaging, needle trays, individual needles, needle caps, needle drivers, needle disposal containers, surgical staff, and/or the patient, as described below. In particular, the computer system can: access a current image of the surgical space captured during the surgery; implement computer vision techniques (e.g., template matching, a convolutional neural network) to detect non-needle objects that frequently contain or interact with needles in this image; and interpret locations of needles in the surgical space based on types and locations of these non-needle objects and/or selectively scan small, select regions of this image—defined relative to these objects—for needle features in order to detect needles depicted in the image directly. The computer system then: interprets a state of each needle detected in this image, such as based on proximity to other surgical tools (e.g., a needle driver), surgical staff (e.g., a scrub tech, an assistant, or a surgeon), or the patient; stores types and locations of objects (e.g., individual object, combinations of objects) detected in the image in a 3D (or 2D) constellation of objects; and writes a timestamp from the image to this constellation of objects. For example, a current object constellation can include a matrix or list of object types and coordinates of visual spatial centroids of these objects in the current image.

In this implementation, the computer system can also: implement object-tracking techniques to track both needles and other objects from preceding images to the current image (or from previous object constellations to the current object constellation); derive velocities of these objects based on their changes in position over sequential images; annotate object representations in the current object constellation with corresponding velocities; and then flag individual needles with non-null velocities for state and risk reassessment. In one example shown in FIGS. 4A and 4B, the computer system can interpret states of individual needles detected in the image—such as "packaged," "in needle tray," "in needle driver," "in disposal container," "loose and unused," or "loose and used"—based on: current and past locations of these individual needles; past states of these individual needles; current and past proximity of these needles to other objects in the surgical space, as represented in object constellations; and/or a predefined sequence of needle states in surgical spaces. The computer system can also interpret a contamination risk (e.g., on a scale from "0" to "100") of each needle detected in the current image, such as based on a current state of an individual needle and current and past proximity of the needle to other objects (e.g., surgical instruments, surgical staff) in the surgical space. The computer system can then annotate representations of individual needles in the current object constellation with their current states and contamination risk values.

The computer system can then store this timestamped object constellation in a surgery file or database affiliated with this surgery. (Alternatively, rather than generate an object constellation based on objects detected in the current image, the computer system can instead annotate the current image with object types, states, velocities, and/or risk values directly and store this annotated image in the surgery file or database affiliated with this surgery.) The computer system can then repeat this process for each subsequent image captured during the surgery.

Additionally or alternatively, the computer system can: detect an individual needle (such as directly or based on locations of a needle driver, a needle package, or a disposal container that contains needles) in images captured by the set of cameras; track the individual needle across these images; aggregate locations of the needle at times corresponding to images in which the computer system detected the needle (or an associated needle driver, needle package, or disposal container); transform these locations into a corpus of timestamped 3D waypoints within the surgical space; and store this set of waypoints as a needle path of the needle. The computer system can subsequently render a 3D needle path—based on these waypoints—over a virtual 3D representation of the surgical space to generate a 3D visualization of movement of this individual needle throughout the surgical space as a function of time during the surgery. The computer system can also annotate these waypoints with contamination risks or sterility scores, injury risks, etc. and can represent locations and/or times within the surgery in which such risks for the individual needle exhibited significant changes.

The computer system can repeat this process for each other needle detected and tracked throughout to generate a corpus of needle paths for needles entering and consumed within the surgical space during the surgery. As described below, the computer system can also derive characteristics or performance metrics of the surgery based on these needle paths, such as: complexity of the surgery proportional to a variance in these needle paths; orderliness of the surgery inversely proportional to the variance in these needle paths; needle handling competence based on contamination and injury risks (or variance thereof between needles consumed during the surgery); efficiency of the surgery inversely proportional to length and/or duration of these needle paths; etc.

4.1 Object Detection in Surgical Space

In one implementation, the computer system implements object detecting, object recognition, and object-tracking techniques to detect non-needle objects in an image of the surgical space. For example, the computer system can: detect quick-response (or "QR") codes or barcodes applied to an inventory table, an operating table, surgical gloves, surgical gowns, surgical face masks, surgical instruments, surgical drapes, surgical sponges, surgical towels, etc.; query a QR or bar code database to identify types of objects to which these QR or bar codes are applied; and populate the current object constellation with locations of these object types. The computer system can also project 2D or 3D boundaries associated with these object types onto the image or into the current object constellation based on locations of corresponding QR or bar codes in the image and then derive distances between objects based on distances between their nearest boundaries. Alternatively, the computer system can implement template matching, edge detection, or other computer vision techniques to extract boundaries of objects from the image once these objects are identified according to these QR or bar codes.

Alternatively, the computer system can extract features from the image and implement template matching, object recognition, or other computer vision techniques to detect and identify objects depicted in the image directly based on these features. For example, the computer system can detect hands of surgical staff by: isolating blue and white regions in the image; implementing object recognition to identify each instance of a hand in white surgical glove; and/or and implementing object recognition to identify each instance of a blue sterile drape grasped by a hand in a white surgical glove. The computer system can also: implement face detection to detect faces of surgical staff and the patient in the image; detect bodies connected to these faces; identify the patient by presence over the operating table; identify the surgeon by proximity to the operating table and facing the patient; and identify an assistant and scrub tech in the image by greater distance from the operating table and/or by closer proximity to the inventory table. In another example, the computer system can implement template matching techniques to detect surgical instruments in the image—such as proximal hands or surgical gloves detected in the image—such as including; a needle driver; a retractor; a knife; scissors; or a clamp.

The computer system can annotate the current object constellation according to the object types detected in the image. The computer system can also implement object-tracking techniques to track these objects in subsequent images captured by the camera.

4.2 Needle in Package

Block S120 of the method S100 recites, in response to detecting a needle package at a first location in a first image in the sequence of images captured at a first time, logging (or "recording") a first needle in a sterile packaged condition at the first location at the first time. Generally, in Block S120, the computer system can detect a sterile needle package—containing a set of trays, each tray containing a set of sterile needles and sutures—in a current image and log presence of a cluster of needles in the surgical space accordingly.

In one implementation as shown in FIG. 3, the computer system identifies this package by detecting a QR code or barcode on the package, reading a label on the package, or matching features in the current image of the surgical space to a template image of a sterile needle package. Upon first detecting this package—such as on or within bounds of an inventory table—the computer system can: retrieve a count of needles contained in the package, such as based on an identifier, QR code, or other value read from the package; and then update a counter for sterile packaged needles in inventory in the surgical space according to this needle count.

The computer system can also update the current object constellation (or update annotations on the current image of the surgical space) to reflect this count of needles at a location of the package detected in the current image. Furthermore, because a sterile needle package is sealed, needles contained in this package may exhibit low contamination risk, low staff risk (i.e., low risk of sticking a surgical staff member), and low retention risk (i.e., low risk of being lost in the surgical space or left in the patient). Therefore, the computer system can label representations of needles in this package in the current object constellation as: in a "packaged" state; in a sterile (or "unused") condition; and exhibiting low contamination, staff, and retention risks.

The computer system can then track this package in subsequent images of the surgical space and implement similar methods and techniques to represent needles in this package in corresponding object constellations.

4.3 Needle in Tool Tray

Later, with the sterile needle package location on the inventory table, the sterile needle package may be opened (e.g., by a scrub tech), and a tray of needles may be removed from the sterile needle package and placed nearby on the inventory table. Accordingly, the computer system can: implement object-tracking to detect and track the tray in a sequence of images of the surgical space as this tray is exposed and removed from the package; retrieve a count of needles per tray in this sterile needle package; decrement the counter for sterile packaged needles in inventory in the surgical space by this count; increment a counter for sterile unpackaged needles in open trays in the surgical space by this count; and increment a counter for total needles consumed in this surgery according to this count of needles in the tray.

The computer system can also: represent this count of needles in the location of the tray in the current object constellation corresponding to a current image captured by the camera; and represent a count of needles in the sterile needle package—less this count of needles in the tray—at the location of the package in the current object constellation. Furthermore, because needles in this tray are currently located on the inventory table and are guarded and retained by the tray, contamination, staff, and retention risks for these needles may remain low. Therefore, the computer system can label representations of needles in this tray in the current object constellation as: in an "unpackaged, in tray" state; in a sterile (or "unused") condition; and exhibiting low contamination, staff, and retention risks.

The computer system can then implement object-tracking techniques to track this tray in a subsequent sequence of frames as the tray is moved with the surgical space, such as from the inventory table to the operating table. As the tray nears the operating table and is handled over time, risk of contamination of needles in the tray may increase. Therefore, in addition to representing locations of the count of needles in subsequent object constellations according to the location of the tray depicted in corresponding images captured by the camera, the computer system can update contamination risk values tagged to these needle representations in these object constellations to reflect this increasing contamination risk.

4.4 Needle in Needle Driver

Block S130 of the method S100 recites, in response to detecting a needle driver at a second location in a second image in the sequence of images captured at a second time succeeding the first time: scanning a second region of the second image depicting a distal end of the needle driver for features representative of the first needle; and logging the first needle in a sterile retained condition proximal the second location at the second time in response to detecting features representative of the first needle in the second region of the second image. Generally, in Block S130, the computer system can detect removal of a needle from the needle tray by a needle driver, track the needle driver and/or the needle—now free from the tray—over a sequence of images as the needle is moved into contact with the patient, and store these new locations and states of the needle in corresponding object constellations.

In one implementation as shown in FIG. 3, the computer system: implements methods and techniques described above to detect hands—in white surgical gloves—in images captured by the camera; isolates regions of the image around each detected hand; and scans each region in the image for features representative of a needle driver. Concurrently, the computer system identifies the needle tray in the image, calculates a distance between the distal end of the needle driver and the needle tray, and repeats this process for subsequent images captured by the camera. Once this distance between the distal end of the needle driver and the needle tray falls below a threshold distance (e.g., two centimeters), the computer system: identifies a distal end of the needle driver in the current image; isolates a subregion of the current image proximal the distal end of the needle driver; and scans this subregion for features representative of a needle. The computer system repeats this process for subsequent images captured by the camera.

Upon detecting a needle at the distal end of the needle driver in a current image, the computer system can: increment a counter for sterile retained needles in needle drivers; decrement the counter for unsterile packaged needles in open trays by one needle; represent this retained needle in the current object constellation according to the location of the distal end of the needle driver detected in the corresponding image; and represent the stock count of needles in the tray—less one—in the current object constellation according to the location of the tray detected in the corresponding image. Furthermore, because this needle is now unguarded and exposed: risk of contamination due to contact with a non-sterile object increases; risk of inadvertent contact with (hereinafter "sticking") a member of the surgical staff increases; and risk of inadvertent release of the needle from the needle driver increases. Therefore, the computer system can label the representation of this retained needle in the current object constellation as: in a "retained by needle driver" state; in a sterile (or "unused") condition; and exhibiting moderate contamination, staff, and retention risks. The computer system can also identify a surgical staff member holding the needle driver in the current image and label the representation of this retained needle in the corresponding object constellation with an identifier of this staff member (e.g., a scrub technician, assistant, or surgeon).

The computer system can then: implement object-tracking techniques to track the needle driver (or the needle itself) in subsequent images captured by the camera; calculate contamination risk for the needle proportional to proximity to other objects in the surgical space and as a function of time since removal from the needle tray and/or proportional to time since removal of the needle from the needle tray; calculate staff risk for the needle proportional to proximity of the needle driver to surgical staff in the surgical space; calculate retention risk for the needle as a function of time since retrieval from the needle tray and/or as a function of velocity through the surgical space; identify the surgical staff member holding the needle driver; and log these characteristics and risk values for the needle in subsequent object constellations as surgical staff prepare to place a suture on the patient with the needle and needle driver.

4.5 Needle Contacting Patient

Block S140 of the method S100 recites, in response to detecting the needle driver at a third location in a third image in the sequence of images captured at a third time succeeding the second time: scanning a third region of the third image depicting the distal end of the needle driver for features representative of a patient; and, in response to detecting features representative of the patient in the third region of the third image, logging the first needle in a used retained condition proximal the third location at the third time. Generally, after retrieving a needle from the needle tray with a needle driver, surgical staff may insert the needle through the patient's tissue around a wound to set a suture on the patient. In Block S140, the computer system can detect and log entry of the needle—retained by the needle driver—into the patient.

In one implementation as shown in FIG. 1, the computer system implements methods and techniques described above to detect the needle driver in an image captured by the camera following retrieval of a needle from the needle tray with the needle driver. Concurrently, the computer system identifies the patient (or the patient's wound) in this image, calculates a distance between the distal end of the needle driver and the patient, and repeats this process for subsequent images captured by the camera. Once this distance between the distal end of the needle driver and the patient falls below a threshold distance (e.g., two centimeters), the computer system: identifies a distal end of the needle driver in the current image; isolates a subregion of the current image proximal the distal end of the needle driver; and scans this subregion for features representative of the patient, the patient's wound, and entry of the needle into the patient's tissue. The computer system repeats this process for subsequent images captured by the camera.

Upon detecting the patient, the patient's wound, and entry of the needle into the patient's tissue at the distal end of the needle driver in a current image, the computer system can: increment a counter for "used" needles; increment a counter for used retained needles; decrement the counter for sterile retained needles by one needle; and represent this used retained needle in the current object constellation according to the location of the distal end of the needle driver detected in the corresponding image. Furthermore, because this needle remains unguarded and exposed but is also now contaminated and ready for disposal: risk of contamination is no longer a meaningful metric; risk of sticking a member of the surgical staff remains high; and risk of inadvertent release of the needle from the needle driver also remains high. Therefore, the computer system can label the representation of this retained needle in the current object constellation as: in a "retained by needle driver" state; in a non-sterile (or "used," contaminated) condition; and exhibiting high staff and retention risks. The computer system can also identify a surgical staff member holding the needle driver in the current image and label the representation of this retained needle in the corresponding object constellation with an identifier of this staff member.

The computer system can then: implement object-tracking techniques to track the needle driver (or the needle itself) in subsequent images captured by the camera; calculate staff risk for the needle proportional to proximity of the needle driver to surgical staff in the surgical space; calculate retention risk for the needle as a function of time since retrieval from the needle tray, proportional to a time in contact with or within a threshold distance of (e.g., ten centimeters) from the patient, and/or as a function of velocity through the surgical space; identify the surgical staff member holding the needle driver; and log these characteristics and risk values for the needle in subsequent object constellations as surgical staff withdraw the needle and needle driver from the patient and prepare the needle for disposal. The computer system can also: track presence and velocity of other objects (e.g., surgical instruments, surgical staff) proximal the patient while a needle is near or in contact with the patient; update retention risk scores for this needle proportional to the velocity of objects near the patient and update staff risk scores for this needle proportional to a quantity of surgical staff near the patient.

4.6 Needle Post-Use: Uncapped

Then, as surgical staff withdraw the needle and needle driver from the patient and prepare to place a cap on the point of the needle, the computer system can: implement object-tracking to detect the needle driver in a next image captured by the camera following use of the needle; detect the distal end of the needle driver in this image; isolate a subregion of the image proximal the distal end of the needle; scan this subregion of the image for the needle and a needle cap; verify that the needle driver retains the needle; calculate staff and retention risks for the needle as described above; and log the state, condition, and location of the needle in the current object constellation as described above. The computer system can repeat this process until a needle cap is detected near the distal end of the needle driver.

For example, as the needle is withdrawn from the patient, the computer system can also track presence and velocity of other objects (e.g., surgical instruments, surgical staff) near the needle as the needle moves throughout the surgical space and update staff risk scores for this needle proportional to a quantity and/or velocity of surgical staff near the needle.

In one variation, the computer system also: accesses thermal images from a thermal camera arranged in the surgical space; projects a boundary around the distal end of the needle driver detected in the (color, photographic) image onto the thermal image based on a known offset between these cameras; scans this region in the thermal image for a temperature gradient indicative of a "hot" needle that was recently inserted into the patient; and verifies presence of the needle in the needle driver responsive to detecting such a temperature gradient.

4.7 Needle Post-Use: Protected

Once the computer system detects a needle cap near the distal end of the needle driver (and determines that the needle cap has obscured or covered the point of the needle) in a next image, the computer system can represent the location of the needle in the current object constellation based on the location of the needle cap. Because the needle is now capped and fixed to a larger, more visible mass (i.e., the needle cap), the computer system can also label this representation of the needle in the current object constellation as: in a capped and retained state; in a non-sterile condition; and exhibiting low staff and retention risks.

The computer system can continue to track the capped needle and to store locations, states, and conditions of the needle in subsequent object constellations as surgical staff move the needle toward needle disposal container.

4.8 Needle in Disposal Container

Block S150 of the method S100 recites, in response to detecting the needle driver at a fourth location in a fourth image in the sequence of images captured at a fourth time succeeding the third time: scanning a fourth region of the fourth image depicting the distal end of the needle driver for features representative of a needle disposal container; and, in response to detecting features representative of the needle disposal container in the fourth region of the fourth image, logging the first needle in a disposed condition proximal the fourth location at the fourth time. Generally, after capping a used needle (or directly after withdrawing the needle from the patient), surgical staff may discard the needle into a needle disposal container, place the needle onto a magnetic disposal strip, or insert the needle into a foam block for subsequent disposal.

In one implementation as shown in FIG. 1, the computer system implements methods and techniques described above to detect the needle driver in an image captured by the camera following placement of a cap on the needle (or as the needle and needle driver are withdrawn from the patient following use). Concurrently, the computer system identifies the needle disposal container in this image, calculates a distance between the distal end of the needle driver and the needle disposal container, and repeats this process for subsequent images captured by the camera. Once this distance between the distal end of the needle driver and the needle disposal container falls below a threshold distance (e.g., two centimeters), the computer system: identifies a distal end of the needle driver in the current image; isolates a subregion of the current image proximal the distal end of the needle driver; and scans this subregion for features representative of the needle and needle driver entering a mount of the needle disposal container. The computer system repeats this process for subsequent images captured by the camera.

Upon detecting the needle and needle driver entering a mount of the needle disposal container in a current image, the computer system can: increment a counter for disposed needles; decrement the counter for used retained needles by one needle; and represent this disposed needle in the current object constellation according to the location of the needle disposal container detected in the corresponding image.

Furthermore, because this needle is now disposed, risk of contamination, risk to staff, and risk of retention are no longer meaningful metrics for this needle. Therefore, the computer system can label the representation of this disposed needle in the current object constellation as: in a "disposed" state; in a non-sterile condition; and exhibiting null contamination, staff, and retention risks.

The computer system can then track this needle—and needles previously disposed during the surgery—by tracking the needle disposal container in images captured during the remainder of the surgery and log locations, states, conditions, and risks of these disposed needles accordingly in subsequent object constellations.

4.9 Needle Stick Event

In one variation, the computer system detects: needle stick events—that is, contact between the point of a needle and surgical staff—based on proximity of the needle (or a needle driver retaining the needle) to surgical staff and movements of the surgical staff; flags such needles accordingly; and records needle stick events in concurrent object constellations.

In one implementation, the computer system implements methods and techniques described above to: track the needle driver; detect the distal end of the needle driver; verify presence of a needle at the distal end of the needle driver; and to detect surgical staff in a sequence of images captured by the camera. The computer system can also calculate distances between the needle or the distal end of the needle driver and surgical staff in these images and flag the need for a possible needle stick event with a particular staff member if this distance falls below a threshold distance (e.g., one centimeter) in a particular image. The computer system can concurrently: track the particular staff member's body or a region of the particular staff member's body proximal the needle across a sequence of images spanning the particular image; derive velocities, accelerations, and/or jerking motion of the staff member's body near the needle driver; and determine whether the particular staff member exhibited a jerking motion based on these velocity, acceleration, and/or jerk values. If the computer system thus detected a jerking motion of the particular staff member around the time that the distance between the needle or the distal end of the needle driver and this jerked region of the staff member's body fell below the threshold distance, the computer system can predict a needle stick event involving the particular staff member.

Accordingly, the computer system can: generate and log a timestamped flag for this needle stick event, including a location of the needle stick event and an identifier of the particular staff member; and issue an audible and/or visual alarm to investigate the needle stick event. The computer system can also: store the location of the needle in the current object constellation; label the needle as in a "retained by needle driver" state, in a contaminated condition, and exhibiting high staff and retention risks; and label the needle as involved in a needle stick event with the particular staff member. Furthermore, the computer system can increment a counter for needle stick events responsive to detecting this needle stick event.

4.10 Loose Needle in Surgical Field

In another variation as shown in FIG. 3, the computer system implements methods and techniques described above to scan images captured by the camera for loose needles in the surgical space, such as present on an inventory tray, on the operating table, or on the floor in the surgical space based on features detected in color photographic or thermal images captured by cameras in the surgical space. For example, the computer system can track removal of a needle from a needle tray and then detect release of the needle onto the inventory table. Accordingly, the computer system can: insert a representation of this needle into the current object constellation; label this representation of the needle as in a "loose, on tray" state and in a sterile condition; assign a moderate contamination risk, low staff risk, and low retention risk to this needle in the current object constellation; and flag this needle for immediate use or disposal. The computer system can also decrement the counter for sterile packaged needles in open trays by one needle and increment a counter for sterile loose needles accordingly.

In another example, the computer system detects a loose needle on the operating table, such as after detecting release or absence of a needle at a distal end of the needle driver. Accordingly, the computer system can: insert a representation of this needle into the current object constellation; label this representation of the needle as in a "loose, on operating table" state and in a non-sterile condition; assign a high retention risk and moderate staff risk to this needle in the current object constellation; and flag this needle for immediate disposal. The computer system can also decrement the counter for retained needles by one needle and increment a counter for loose needles accordingly. The computer system can similarly detect and respond to a needle present on a floor of the surgical space or present on a textile (e.g., clothing, a surgical drape, a surgical sponge).

In this variation and as described below, the computer system can also render prompts on a display in the surgical space or activate an audible alarm to prompt surgical staff to retrieve a loose needle, continue to track the loose needle, and automatically deactivate this prompt or alarm in response to detecting retrieval of this loose needle. The computer system can also render a map or image of the surgical space annotated with a location of this loose needle in order to guide surgical staff in finding and retrieving this loose needle.

The computer system can implement similar methods and techniques to detect broken needles and to prompt retrieval and disposal of broken needles.

4.11 Needle Loss Event

Similarly, after detecting a needle at the distal end of a needle driver, the computer system can implement methods and techniques described above to track this needle driver and to verify presence of the needle at the distal end of the needle driver. If the computer system later detects—in an image captured by the camera—that the needle is no longer present at distal end of needle driver (e.g., for more than a threshold duration or threshold quantity of consecutive images) and the needle driver is not proximal the patient, a needle cap, or a needle disposal container, the computer system can interpret this transition from presence of the needle to absence of the needle at the needle driver as a needle loss event.

Accordingly, the computer system can: identify a last image that depicts the needle in contact with the needle driver; insert a representation of this needle in the current object constellation; label this location in the current object constellation as a last retained location of this needle; label this needle in the current object constellation as "lost"; assign high staff and retention risks to this needle in the current object constellation; increment a counter for lost needles; decrement a counter for sterile or used retained needles based on the last "sterile" or "used" state of this needle; and activate an alarm to retrieve or investigate for the lost needle.

For example, after logging entry of a sterile needle package at the inventory table, the computer system can: initialize new logs for a known quantity of needles stored in a type of the needle package; and track the needle package and individual ends removed from the needle package over subsequent images captured by a first set of optical sensors arranged over the inventory table. Upon detecting a needle driver entering the field of view of the first set of optical sensors, the computer system can: detect and track the needle driver in subsequent images captured by the first set of optical sensors; and scan region of images—captured by the first set of optical sensors—around a distal end of the second needle driver for features representative of a needle in Block S130. In response to detecting features representative of a needle proximal—that is, contacting or within a threshold distance (e.g., 2 millimeters) of—the distal end of the needle driver, the computer system can: update a log for a first needle to reflect a change in status to a "sterile retained condition" at the current time; decrement a sterile packaged counter; increment a sterile retained counter, and then track the needle driver in subsequent images captured by the first set of optical sensors. The computer system can concurrently: scan images captured by the third set of optical sensors—arranged over the intermediate field in the surgical space—for the needle driver; track the needle driver from images captured by the first set of optical sensors to images captured by the third set of optical sensors; and scan regions of images in these feeds for features representative of a needle (e.g., heat signature, high reflectivity in a narrow arc) near the distal end of the needle driver. Accordingly, the computer system can verify retention of the first needle in the needle driver based on presence of such needle features proximal the distal end of the needle driver in these images. However, in response to detecting absence of features representative of a needle proximal the distal end of the needle driver in a particular image captured by the third set of optical sensors, the computer system can: detect loss of the first needle from the needle driver at the current time and within the intermediate field; and activate an audible and/or visual alarm for loss of the first needle, thereby prompting surgical staff to search for and retrieve the first needle driver.

In this example, the computer system can also: indicate loss of the first needle in the intermediate field and prompt surgical staff to prioritize investigation of surfaces within the intermediate field for loss of the first needle; and update the log of the first needle to reflect a loss event in the intermediate field of the surgical space. Additionally or alternatively, the computer system can: calculate a probability map of locations of the first needle at the current time based on the location and orientation of the needle driver in the surgical space when the computer system detected the loss event; and presenting this probability map to surgical staff, such as via a fixed display arranged in the surgical space and/or via an augmented reality headset worn by a surgical staff member in the surgical space. For example, the computer system can access a predefined needle trajectory model that: generates many (e.g., thousands of) possible ballistic trajectories of a needle based on needle driver orientation, height of the needle driver above a floor, and locations of nearby surfaces relative to the needle driver; and compiles these possible ballistic trajectories into a probability map—such as in the form of a "heatmap" or "gradient"—of possible landing locations of needles. The computer system then: extracts the 3D position of the needle driver from the last image in which the needle was detected proximal (e.g., within contact of) the needle driver; detects surfaces near the needle driver in this image; approximates these surfaces as planar surfaces; extracts positions of these planar surfaces relative to the needle driver from this image; and inserts these values into the needle trajectory model. The needle trajectory model then generates a probability map, and the computer system renders this probability map to surgical staff, such as via a fixed display or augmented reality headset(s) in the surgical space. Surgical staff may then review this probability map and prioritize investigation of the surgical space for the first, lost needle according to regions in the probability map indicating greatest probability of the current location of the first needle.

The computer system can implement similar methods and techniques: to detect and track a needle and needle driver transitioning from the intermediate field into the operating field and/or back to the inventory field; and to log and prompt investigation into a needle lost from a needle driver in real-time.

4.12 Multiple Needles in Multiple States

The computer system can execute the foregoing methods and techniques to detect, track, and assess multiple (e.g., tens, hundreds) of needles (and other objects) in an image (or across multiple concurrent images) of the surgical space and to log these data in an object constellation representing the surgical space at the time this image(s) was captured. The computer system can also repeat this process for each other image captured by the camera (or set of concurrent images captured by the set of optical sensors) to generate a timeseries of locations, states, conditions, and risk values for many needles (and/or other objects) present in the surgical space throughout the surgery.

5. Real-Time Counters

Throughout the surgery, the computer system can render current states of various needle-related counters on a display in the surgical space, such as counters for: packaged needles in inventory; packaged needles in opened trays; retained sterile needles (e.g., a total count of sterile needles currently retained by needle drivers); used retained needles; used, capped, and retained needles; disposed needles; needle stick events; loose needles; lost needles; and total needles consumed (i.e., a count of all unpackaged needles brought into surgical space), as shown in FIGS. 2, 3, 4A, and 4B. The computer system can thus enable surgical staff to quickly access counts of needles in various states within the surgical space during the surgery.

Furthermore, upon conclusion of the surgery or in preparation for a shift change during the surgery, the computer system can prompt surgical staff to verify a target needle condition in the surgical space by driving counters for retained sterile needles, used capped needles, loose needles, and lost needles to null and by ensuring that a counter of needles in the needle disposal container equals a count of needles removed from all needle trays. Alternatively, by rendering these counters on the display, the computer system can enable a next surgical staff or janitorial staff to immediately review quantities and states of needles in the surgical space.

5.1 Variation: Inventory Field Camera

In one variation as shown in FIG. 3, the computer system can: access images from a single camera (or a single set of cameras) arranged in the inventory field and facing the inventory table; detects entry of needle packages, opened needle packages, loose needles, entry of needle drivers and used needles, removal of needle drivers and sterile needles from the inventory field, and disposal of used needles in these images; and generate a log of states, state changes, and locations of needles entering, occupying, and leaving the inventory field accordingly. The computer system can then generate and present needle counters to surgical staff in real time during the surgery based on these needle locations and states, such as including: a sterile packaged needle counter; a sterile unpackaged needle counter; a sterile loose needle counter; a sterile retained needle counter; a deployed needle counter (e.g., when a needle driver retaining a needle is withdrawn from the inventory field); a returned retained used needle counter (e.g., when a needle driver retaining a needle is returned to the inventory field); and/or a returned used contained needle counter (e.g., when a needle returned to the inventory field is placed in a disposal container or back into a needle package or needle tray).

For example, during the surgery, the computer system can access a first sequence of images captured by a set of optical sensors arranged over and facing the inventory table in Block S110 and scan the sequence of images for features representative of needle packages and needles in Block S120. Then, in response to detecting entry of a needle package into surgical space at a first time, the computer system can: detect an identifier (e.g., a barcode) of the needle package or otherwise identify a type of the needle package based on the first sequence of images; retrieve a count of needles—contained in the needle package—associated with the identifier or type of needle package, such as from an inventory database; log entry of the needle package—labeled as sterile—into the inventory field at the first time in Block S120; and increment a sterile packaged needle counter by the count of needles associated with the identifier or type of the needle package in Block S122.

The computer system can: continue to scan images captured by the first set of optical sensors for removal of packing material from the needle package and then increment a sterile unpackaged needle counter and decrement the sterile packaged needle counter by the count of needles associated with the needle package upon detecting the needle package in an opened state. The computer system can then scan regions of images—captured by the first set of optical sensors—around the needle package for features representative of needles; and increment a sterile loose needle counter and decrement the sterile unpackaged needle counter by one needle in response to detecting features representative of an individual needle beyond a threshold distance (e.g., 5 millimeters) from the needle package and within the boundary of the inventory field and beyond a threshold distance (e.g., 5 millimeters) from a needle driver.

The computer system can similarly: scan these images for needle drivers; and increment a sterile retained needle counter and decrement the sterile unpackaged needle counter by one needle in response to detecting a distal end of a needle driver approaching the needle package, contacting the needle package, and then withdrawing from the needle package with features representative of a needle proximal and moving with the distal end of the needle package. The computer system can also increment a sterile retained needle counter and decrement the sterile loose needle counter by one needle in response to detecting a distal end of a needle driver approaching a stored location of a loose needle on the inventory table, pausing at this stored location, and then withdrawing from this stored location with features representative of a needle proximal and moving with the distal end of the needle package.

Subsequently, the computer system can track the needle driver—and verify presence of features representative of a needle near the distal end of the needle driver—moving within the inventory field. Upon detecting transition of the needle driver out of the inventory field (e.g., beyond the field of view of the first set of optical sensors and/or into the field of view of the third set of optical sensors described above), the computer system can increment a deployed needle counter in Block S132.

Later, upon detecting that the needle driver (e.g., any needle driver or a needle driver uniquely identified by a barcode or other optical fiducial on the needle driver) was returned to the inventory field based on images captured by the first set of optical sensors, the computer system can: scan these images for features representative of a needle near the distal end of the needle driver; increment a returned retained used needle counter; and decrement the deployed needle counter accordingly.

The computer system can: continue to track the needle driver in these images; and detect and track a needle disposal container in the inventory field or otherwise scan these images for the needle disposal container near the distal end of the needle driver in Block S150. Then, in response to detecting the needle driver inserted into the needle disposal container, detecting the needle driver within a threshold distance (e.g., 2 millimeters) of the needle disposal container, and/or verifying absence of needle features near the distal end of the needle driver following retracting of the needle driver from the needle disposal container, the computer system can: log the needle in a disposed condition; and increment a used contained needle counter accordingly.

5.2 Needle Package Status

In one variation in which the surgical staff return used needles back to a needle package (e.g., to a needle tray within the original needle package), the computer system can also track used needles reentering the inventory field and update the status of the needle package—and any unused needles remaining in the needle package—to "unsterile" (or low sterility probabilities) if a used needle is returned to the needle package and update logs and counters for the surgery accordingly.

For example, in response to detecting return of a used needle to the inventory field—such as by detecting a needle driver returning to the inventory field and verifying presence of needle features tracking with the distal end of the needle driver—the computer system can: label the needle "used" and "retained" but "uncontained" at the current time; and track the needle in subsequent images captured by the first set of optical sensors. Then, in response to detecting insertion of the needle driver into the needle package or otherwise detecting the needle driver within a threshold distance (e.g., 2 millimeters) of the needle package, the computer system can: associate the needle with the needle package; re-label the needle package as unsterile to reflect presence of a used needle in the needle package and possible contamination of any other remaining needles in the needle package; increment a contained used needle counter for the needle; retrieve a value of a sterile packaged needle counter—representing a total number of unused, sterile needles remaining in the needle package prior to insertion of the used needle—at the current time; increment the contained used needle counter by the value of a sterile packaged needle counter to reflect a new "used, contaminated" state of any remaining needles in the needle package; and clear the sterile packaged needle counter to "null" or "zero" for the needle package.

5.3 Needle Tracking in Operating and Intermediate Fields

In the variation described above in which the computer system tracks needles entering and leaving the inventory field based on images captured by the first set of optical sensors over the inventory field only, the computer system can implement a "first out, first in" paradigm to link events of needles leaving and then re-entering the inventory field and thus maintain individual logs of states and locations of all needles consumed during the surgery. Additionally or alternatively, the computer system can detect and distinguish individual needles leaving and re-entering the inventory field by uniquely identifying needle drivers leaving and re-entering the inventory field—with retained needles—such as by detecting unique barcodes, quick-response codes, or other unique optical identifiers arranged on these needle drivers (and based on an assumption that a needle remains paired within one needle driver while deployed on the surgical space).

Alternatively, in the variation described above in which the computer system interfaces with multiple optical sensors (or multiple sets of optical sensors) defining overlapping fields of view that extend from the inventory field to the operating field, the computer system can: continuously track needle drivers moving between the prep, intermediate, and operating fields; track locations of individual needles from entry into the inventory field via a needle package to use within the operating field to disposal in the operating, intermediate, or inventory field; and thus maintain complete logs of locations, retention and sterility conditions, and risks of individual needles from entry into the surgical space to disposal during the surgery.

6. Needle Management Alarms

In one variation as shown in FIGS. 1, 2, 4A, and 4B, the computer system can issue other alarms based on needle retention, needle loss, and other needle-related risks during the surgery.

In one implementation, the computer system issues an alarm in response to deployment of a needle exceeding a threshold duration of time. For example, the computer system can: log deployment of a needle at a first time upon detecting removal of the needle from the inventory field; set a timer for a threshold deployment duration (e.g., two minutes); clear the timer in response to detecting return of the needle to the inventory field (e.g., by uniquely identifying a needle driver retaining the needle returning to the inventory field; by tracking the needle continuously between the inventory and operating fields); and activate an audible and/or visual needle loss alarm in response to expiration of the timer prior to return of the needle to the inventory field. Responsive to the alarm, surgical staff may search the patient and the operating field for a loose needle, thereby reducing risk of a retained needle in the patient.

In another implementation, the computer system issues an alarm in response to concurrent deployment of more than a threshold quantity of needles in the surgical space. For example, the computer system can implement methods and techniques described above to maintain deployed and returned used needle counters during the surgery. Thus, in response to the deployed needle counter, a threshold quantity of (e.g., three) needles—such as at any time or for more than a threshold duration of time (e.g., 20 seconds, such as to accommodate a needle and needle driver exchange at the inventory table)—the computer system can: issue an audible and/or visual alarm for manual survey of needles in the surgical space; and serve a prompt to surgical staff in the surgical space to return a quantity of loose needles, equal to a difference between the deployed needle counter and the threshold quantity of needles, to the needle disposal container.

In another implementation, the computer system: tracks a needle in a sequence of images captured during the surgery; monitors proximity of the needle to the patient following initial entry of the needle into the inventory field; calculates a series of retention risks for retention of the needle in the patient based on (e.g., proportional to) proximity of the needle to the patient integrated over time from unpacking of the needle until disposal of the needle in a disposal container; generates an audible and/or visual alarm in response to the retention risk of the needle exceeding a threshold risk; and augments a path of the needle—represented in a log file—with the series of retention risks for retention of the needle in the patient and the location of the needle at the time of the alarm. Responsive to this alarm, surgical staff may: elect to mute the alarm if the needle is intentionally held in reserve near a surgeon or intentionally remaining in place inside the patient; or otherwise retrieve and discard the needle, thereby reducing risk of a retained needle in the patient.

In another implementation, the computer system: tracks a needle in a sequence of images captured during the surgery; detects proximity of the needle to the patient, surgical staff, and other surfaces of known, predicted, or characterized sterility following initial entry of the needle into the inventory field; calculates a sequence of contamination risks for loss of sterility of the needle based on proximity of the needle to the patient, surgical staff, and other surfaces of known sterility integrated over time; generates an audible and/or visual alarm in response to the contamination risk of the needle exceeding a threshold risk; and augments a path of the needle—represented in a log file—with the series of contamination risk of the needle and the location of the needle at the time of the alarm. Responsive to this alarm, surgical staff may elect to discard the needle and retrieve a new, sterile needle instead, thereby reducing risk of infection to the patient.

7. Real-Time Needle Map

Figure 4A:
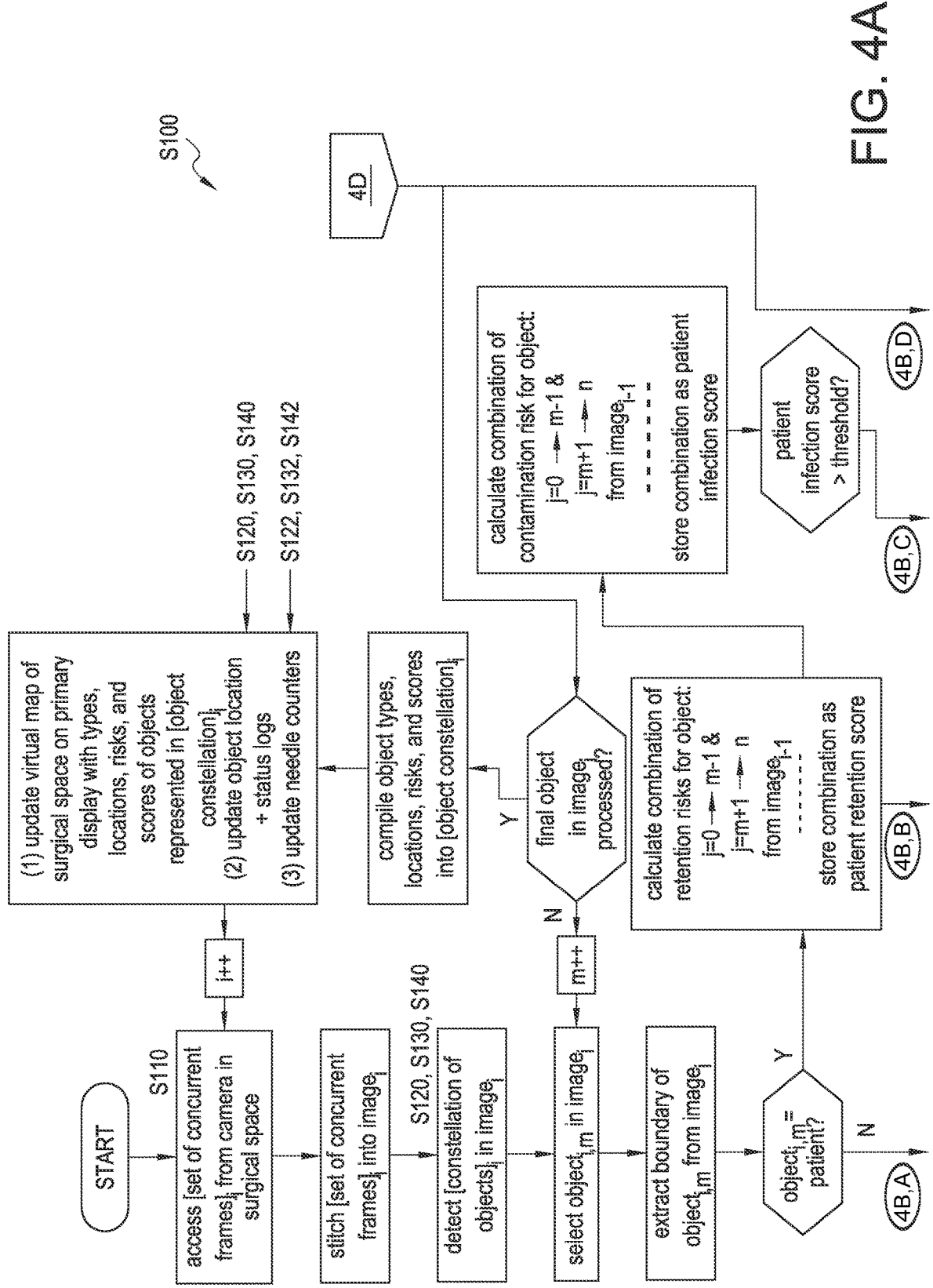
Figure 4B:
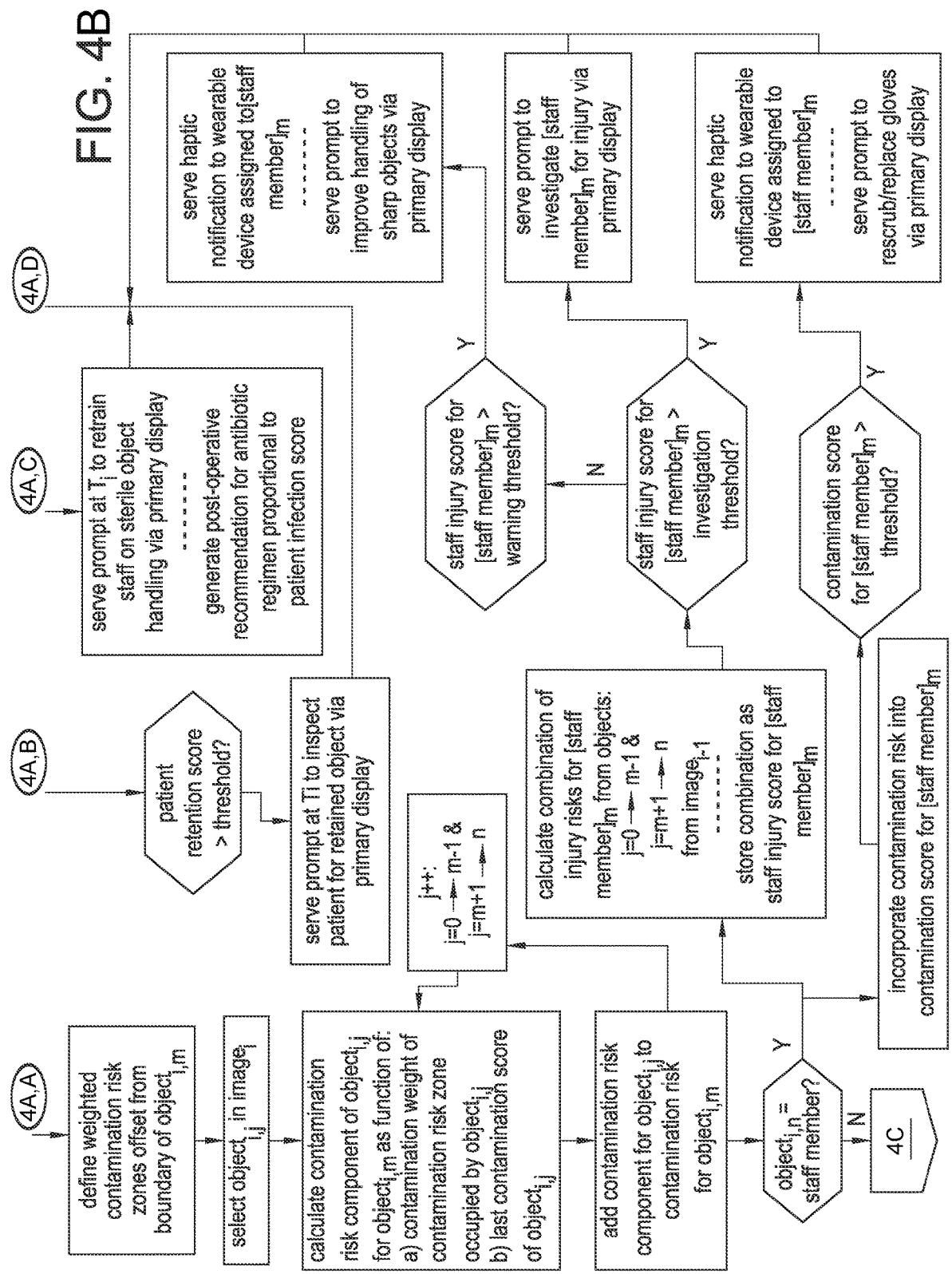
Figure 4D:
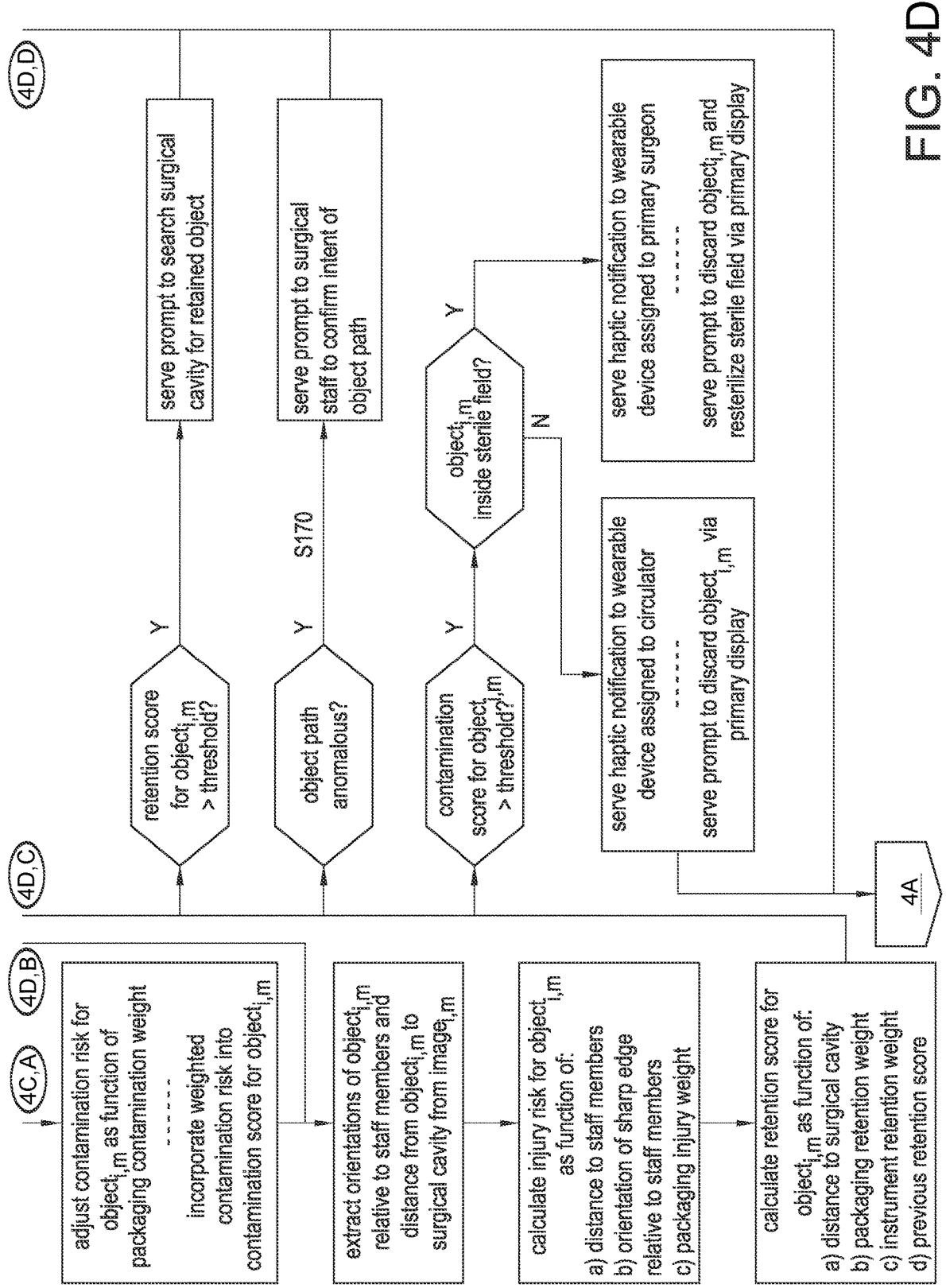

Throughout the surgery, the computer system can also overlay needle markers on a map of the surgical space at locations of needles detected in a current image captured by the camera and render this annotated surgical space map on the display in the surgical space, as shown in FIGS. 4A and 4B. For example, the computer system can set colors of needle markers in this map according to states, contamination risks, and/or staff risks of corresponding needles, such as by representing these states and conditions with concentric circles, colored according to these parameters around each needle marker in the map. In another example, the computer system can animate select needle markers on the map, such as by: flashing a purple needle marker representative of a needle that pricked a staff member; or flashing a colored (e.g., blue) needle marker representative of a needle detected on the floor of the surgical space.

Alternatively, the computer system can annotate the current image captured by the camera with such needle markers and render this annotated image on the display. Yet alternatively, the computer system can render a gradient of needle density throughout the space—such as weighted by contamination, staff, and/or retention risk—over the map or image of the surgical space and display this annotated map or image on the display.

The computer system can thus interface with a display in the surgical space to enable surgical staff to quickly visualize locations of needles and their states within the surgical space.

8. Real-Time Insights

The computer system can also derive real-time insights from needle-related data contained in object constellations thus generated during the surgery, as shown in FIGS. 3, 4A, and 4B.

For example, the computer system can: extract time-stamped locations of an individual needle from these time-stamped object constellations; aggregate and order these timestamped locations into a path of the individual needle through the surgical space during the surgery; and repeat this process to calculate paths of each other needle moving through the surgical space during the surgery. The computer system can compare each needle path—in real-time—to previous needle paths recorded during this surgery and/or recorded during similar past surgeries performed in this surgical space in order to identify anomalous needle paths. The computer system can then activate a visual or audible flag for an anomalous needle path in order to prompt surgical staff to investigate and correct use of the corresponding needle.

In another example, the computer system can track times that individual needles in the surgical space spend in different states—such as in packages, in trays, unused and retained in a needle driver, used and retained in a needle driver, and capped while retained in a needle driver—and render these times on the display, such as in real-time for each needle not currently contained in either a needle tray or needle disposal container. The computer system can also: retrieve similar time values for needles consumed in similar past surgeries performed in the surgical space and/or performed by the same surgeon; flag specific needles that deviate significantly in time spent in such states compared to these historical data; and prompt surgical staff to investigate these specific needles in (near) real-time during the surgery.

In a similar example, the computer system can: calculate average, maximum, and/or minimum times and/or time variances from retrieval of needles until use of these needles or until disposal of these needles in a needle disposal container, such as for individual needles and/or for all needles consumed during the current surgery based on needle paths described above; and render these time values on the display. The computer system can also retrieve similar time values (or time value ranges) for needle consumption in similar past surgeries, such as performed in the surgical space and/or performed by the same surgeon. The computer system can then render these historical time values—for reference—on the display or highlight time values for needle consumption during the current surgery that deviate by more than a threshold duration from these historical time values, thereby enabling surgical staff to quickly ascertain their performance and efficiency during the current surgery.

In another implementation, the computer system derives trends in needle consumption during the current surgery based on data contained in object constellations. For example, the computer system can calculate a rate of needle consumption (e.g., in needles per minute) based on times that needles are first removed from a tray and loaded into a needle driver or based on times that needles are first brought into contact with the patient. The computer system can also extrapolate future consumption of needles during the surgery and predict a future time that additional sterile needles will no longer be available in needle trays present in the surgical space. For example, the computer system can: predict a future time that a sum of counters for packaged needles and needles in opened trays will reach zero; render a countdown timer to this future time on the display; and then render a visual and/or audible prompt to bring a next package of needles into inventory once a time on the countdown timer is less than a threshold duration (e.g., a maximum or average time to retrieve a package of needles and to remove a tray of needles from this package, such as four minutes).

In yet another implementation, the computer system indicates needle risk on the display. For example, as an individual needle is exposed at a needle tray, moves through the surgical space, and is eventually disposed in a needle disposal container, the computer system can integrate contamination risk associated with the individual needle over time and store this value as a needle contamination risk score for this individual needle. In this example, the computer system can also: sum needle contamination risk scores for this needle and all preceding needles consumed during the surgery; pass this sum through a contamination model (e.g., a statistical model) to predict likelihood of infection in the patient resulting from needle handling in the surgical space; and render a value representative of this likelihood on the display. The computer system can also output a visual or audible prompt to pause the surgery and audit needle handling in the surgical space if this value for infection risk to the patent—resulting from needle handling—exceeds a threshold probability (e.g., 50%). The computer system can implement similar methods and techniques to track aggregate staff risk for needles moving through the surgical space and to render this aggregate staff risk on the display during the surgery.

However, the computer system can derive any other insights or metrics for needle consumption during the current surgery in (near) real-time based on data stored in object constellations derived from a live feed of images of the surgical space and can present these insights and metrics to surgical staff in any other format.

9. Post-Operative Insights

The computer system can similarly derive post-operative insights from these object constellations and needle consumption data, as shown in FIGS. 2, 4A, and 4B. For example, the computer system can score efficiency and complexity of the surgery, sterility management of needles during the surgery, consumption of needles, and/or injury related to needle use during the surgery, etc. based on these object constellations and needle consumption data. The scores derived by the computer system may thus represent benchmarking metrics for cases, surgeons, hospitals, and/or hospital systems, etc.

9.1 Needle Path Variance

In one implementation show in FIG. 2, the computer system calculates spatial and temporal variance of paths of individual needles consumed during the surgery and calculates an average retention time from removal of needles from a needle tray to use of these needles at the patient (or to disposal of these needles). The computer system can then quantify an efficiency of the surgery: inversely proportional to these spatial and temporal variances; inversely proportional to the average retention time; and/or inversely proportional to a number of needle loss events during the surgery. The computer system can also quantify a complexity of the surgery: proportional to a total quantity of needles consumed; proportional to a ratio of total needles used at the patient to total quantity of needles consumed; and/or proportional to variance in location of initial contact between needles and the patient (which may be a measure of a size of a wound) during the surgery. The computer system can also quantify an efficacy of the surgical staff, such as: inversely proportional to a quantity of needle stick events; inversely proportional to a quantity of needle loss events; inversely proportional to a ratio of total consumed needles to a quantity of needles brought into inventory; and/or inversely proportional to total duration of needle out-of-stock periods in the surgical space during the surgery. In this implementation, the computer system can also flag this surgery or this surgical staff for post-operative review if these efficiency, complexity, and efficacy metrics for this surgery and surgical staff deviate significantly from historical metrics for similar surgeries or surgical staff. Accordingly, a reviewer may access and review an image feed and/or a timeseries of object constellations recorded during the surgery.

9.2 Post-Operative Review

The computer system can also flag periods of the surgery in which a subset of needles within the surgical space traversed anomalous paths through the surgical space and then prompt a reviewer to specifically review these periods of the surgery. The computer system can then selectively serve clips of the image feed and/or timeseries of object constellations corresponding to these flagged periods during the surgery to a reviewer portal to enable the reviewer to quickly access and review periods of the surgery most likely to depict errors or opportunities to improve surgical efficiency.

9.3 Post-Operative Patient Care

In another implementation shown in FIGS. 3 and 4A, the computer system can selectively prompt post-operative assessment of the patient at a frequency or scale based on efficiency, complexity, and/or efficacy of the surgery or surgical staff. For example, the computer system can prompt hospital staff to plan for a post-operative hospital stay for the patient and/or schedule follow-up frequency for the patient proportional to surgery complexity and inversely proportional to surgery efficiency and surgical staff efficacy. In another example, the computer system can prompt hospital staff to initiate a post-operative antibiotic regimen for the patient based on an aggregate contamination risk of needles consumed during the surgery, based on a quantity of needle stick events, and/or based on a quantity of needle loss events during the surgery.

In one example, variance of needles paths, used needle quantity, needle deployment duration, needle retention risk, needle contamination risk, stick events, needle deployment duration variance, etc. may predict complexity of a surgery, orderliness of a surgery, retention and infection risk to a patient, and thus an outcome for the patient. Thus, the computer system can: aggregate logs of locations and conditions of a first needle—such as stored in a first log file specific to this first needle—into a first 3D path of this needle throughout the entire surgery in Block S160; derive other metrics for the first needle from the first log file, such as deployment duration; repeat this process for each other needle consumed during the surgery; and calculate or characterize a path variance between needle paths of these needles, variance in needle deployment duration, and/or total count of needles consumed, etc. during the surgery.

In this example, the computer system can then access a patient outcome model that links variance in needle paths, needle quantity, needle deployment duration, and/or needle deployment duration variance, etc.) to patient outcome (e.g., infection rate, hospitalization time, morbidity, retained needle rate, retained sponge rate). The computer system can then pass needle-based metrics of the surgery into the patient outcome model, which then returns a prediction for a scope (e.g., type and magnitude) of post-operative complications for the patient.

Additionally or alternatively, the computer system can characterize needle paths during the surgery and compare these needle path characteristics to needle paths of other past surgeries with known patient outcomes (e.g., recovery rates, recovery durations, post-operative complications, morbidity rates, infection rates, hospital stay lengths) to predict the outcomes for the patient for the current surgery. For example, the computer system can: calculate a characteristic (e.g., path variance, average deployment duration, deployment duration variance) of the set of needle paths captured during the surgery; access a type of the surgery (e.g., knee replacement, spinal trauma); access a first characteristic of a first corpus of needle paths recorded during a first set of past surgeries, of the same type, associated with a low magnitude of post-operative patient complications; access a second characteristic of a second corpus of needle paths recorded during a second set of past surgeries, of the same type, associated with a high magnitude of post-operative patient complications; predict a scope of recovery (e.g., recovery magnitude and duration) for the patient based on proximity of the characteristic of the set of needle paths of the current surgery to the first characteristic; and predict a scope of post-operative complications (e.g., type and magnitude or complications) for the patient based on proximity of the characteristic of the set of needle paths of the current surgery to the second characteristic. In a similar example shown in FIG. 2, the computer system can: represent needle path metrics derived from needle paths and/or represent individual needle paths captured during the current surgery in a vector; retrieve similar vectors representative of other past surgeries and labeled with known outcomes of these surgeries; implement nearest neighbor, regression, or clustering techniques, etc. to identify a subset of past surgeries exhibiting needle paths most similar to the current surgery; and then predict an outcome (or a set of possible outcomes) of the current surgery based on known patient outcomes associated with this subset of past surgeries.

The computer system can then return this prediction to surgical staff following completion of the surgery in order to guide a follow-up schedule, monitoring, or further post-operative treatment for the patient. For example, the computer system can prompt surgical staff to increase monitoring for patient infection responsive to variance in needle paths and aggregate contamination risks of all needles exceeding threshold values. Additionally or alternatively, the computer system can return this prediction to surgical staff in real-time during the surgery in order to prompt the surgical staff to execute actions that may ameliorate such post-operative complications for the patient.

9.4 Surgery Metrics

In the foregoing example, the computer system can also: score a complexity of the surgery proportional to variance in needle deployment duration; score an orderliness of the surgery inversely proportional to variance in needle deployment; and/or score a quality of the surgery inversely proportional to the sum of retention and contamination scores for all used needles and/or inversely proportional to a quantity of needle stick events; etc. The computer system can then label records for the surgery accordingly and/or prompt further investigation of the surgery in response to one or multiples of these metrics deviating from a target range, as shown in FIG. 2.

9.5 Intent

In another implementation as shown in FIGS. 2 and 4B, the computer system: detects an anomalous needle path; flags the anomalous needle path; and prompts surgical staff to indicate intent and log other notes related to the anomalous needle path. More specifically, by flagging anomalous needle paths and prompting surgical staff to indicate whether such anomalies during the surgery were intentional, the computer system can: log and capture intentional changes and experimentation within the surgical space; and flag surgical staff for training if such anomalies were unintentional.

For example, upon conclusion of the surgery, the computer system can: access a type of the surgery; access a corpus of needle paths recorded during a set of past surgeries of the same surgery type (and occurring with the same surgeon or surgical staff, within the same operating room, within the same hospital, within the same hospital group, within the same geographic region, and/or within the same country); and characterize a difference between the set of needle paths captured during the surgery and the corpus of needle paths captured during the set of past surgeries. In this example, the computer system can calculate: an average, maximum, minimum, and variance of needle paths and deployment durations for the current surgery; retrieve or calculate similar metrics for the set of past surgeries; and calculate a composite score that represents differences between these values across the current and past surgeries. If this difference exceeds a threshold difference, then the computer system can prompt surgical staff to confirm intent of the difference (i.e., whether differences between needle paths during the current surgery and past like surgeries was intentional or accidental). The computer system can also generate and serve a visualization of the surgery to surgical staff associated with the surgery, such as by: retrieving logs of needles consumed during the surgery; constructing 3D needle paths from timeseries needle locations extracted from these logs; and rendering each 3D needle path captured during the surgery in an ordered series within a 3D virtual representation of the surgical space or by concurrently overlaying all such 3D needle paths over the 3D virtual representation of the surgical space, thereby enabling surgical staff to review all needle paths and related events during the surgery. Alternatively, the computer system can selectively render—sequentially or concurrently—a subset of needle paths that represent the most significant anomalies within the current surgery or between the current surgery and the set of past surgeries, thereby enabling the surgical staff to focus attention to these anomalous needle paths.

If the surgical staff confirms intent of the anomalous needle paths, then the computer system can: prompt the user to submit a note or "remark" describing the intent of the anomaly; and then link this note with the surgery, such as by writing the note to a surgery file for the surgery. Conversely, if the surgical staff indicates that the anomalous needle paths were unintentional, the computer system can prompt or schedule needle handling training for the surgical staff.

In this implementation, the computer system can also derive a correlation between: a change in patient outcome and/or efficiency of the surgery; and an intentional anomaly in needle path during the surgery. For example, the computer system can characterize efficiency of the surgery, such as: proportional to orderliness and complexity of the surgery, as described above; based on the duration of the surgery relative to durations of other similar surgeries; and/or inversely proportional to a quantity of needles consumed during the surgery; etc. The computer system can also characterize efficacy of the surgery based on patient outcome, such as inversely proportional to a hospital stay, post-operative infection severity, and/or recovery time, etc. of the patient, such as relative to other patients experiencing similar surgeries. Then, the computer system can predict a strength of correlation between these anomalous needle paths and efficiency and/or efficacy of the surgery, such as: inversely proportional to a variance between (or proportional to a consistency of) needle paths during the current surgery; and proportional to magnitude of the change in efficiency or efficacy of the surgery relative to other surgeries of the same type.

If this correlation exceeds a threshold score and if the surgical staff confirmed intent of the anomalous needle path, then the computer system can prompt investigation of these anomalous needle paths—captured during the surgery—for a possible improvement to a needle handling process in the surgical space.

Therefore, the computer system can: both detect and log intent of an anomalous needle path captured during the surgery; correlate an anomalous needle path with a change in efficiency and/or efficacy of the surgery; and flag the surgery for investigation—such as to expand development of new needle handling processes that may improve efficiency and/or efficacy and to shutter new needle handling processes that may reduce efficiency and/or efficacy—based on intentional needle path anomalies correlated with such changes. Thus, the computer system can automate knowledge capture and experimentation logging in order to support refinement of processes within the surgical space based on needle paths captured during surgeries occurring over time within the surgical space (and/or within many other surgical spaces and/or with the same or other surgical staff).

10. Modeling

In another variation, the computer system: accesses outcomes of surgeries (e.g., patient recovery durations, patient infection rates, staff infection rates from needle stick events); retrieves needle consumption data and metrics from these surgeries; and implements statistical methods, regression, and/or other techniques to develop models (e.g., statistical models) linking these needle consumption data and metrics to surgery outcomes. For example, the computer system can: derive a correlation between aggregate contamination risk for needles consumed during past surgeries and patient infections following these past surgeries; and then leverage this correlation to selectively prompt or inform post-operative antibiotic regimens for future patients based on aggregate contamination risk for needles consumed during corresponding future surgeries. In another example, the computer system can: derive a correlation between aggregate staff risk for needles consumed during past surgeries and needle stick events during these past surgeries; and then leverage this correlation to selectively prompt surgical staff to pause a future surgery and audit needle handling practices in real-time during this future surgery based on aggregate staff risk for needles consumed during this future surgery.

However, the computer system can implement any other method or technique to develop models linking needle consumption with a surgery to an inter-operative or post-operative outcome for patients and surgical staff and then leverage such models in any other way to inform inter-operative or post-operative patient and surgical staff care.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for monitoring needle consumption in a surgical space during a surgery includes:
    accessing a sequence of images of a surgical space captured by a set of optical sensors arranged in the surgical space;
    in response to detecting a needle package at a first location in a first region of a first image, in the sequence of images, captured at a first time, logging a first needle in a sterile packaged condition at the first location at the first time;
    in response to detecting a first needle driver at a second location in a second image, in the sequence of images, captured at a second time succeeding the first time:
        scanning a second region of the second image depicting a distal end of the first needle driver for features representative of the first needle; and
        in response to detecting features representative of the first needle in the second region of the second image, logging the first needle in a sterile retained condition proximal the second location at the second time;
    in response to detecting the first needle driver at a third location in a third image, in the sequence of images, captured at a third time succeeding the second time:
        scanning a third region of the third image depicting the distal end of the first needle driver for features representative of a patient; and
        in response to detecting features representative of the patient in the third region of the third image, logging the first needle in a used retained condition proximal the third location at the third time;
    in response to detecting the first needle driver at a fourth location in a fourth image, in the sequence of images, captured at a fourth time succeeding the third time:
        scanning a fourth region of the fourth image depicting the distal end of the first needle driver for features representative of a needle disposal container; and
        in response to detecting features representative of the needle disposal container in the fourth region of the fourth image, logging the first needle in a disposed condition proximal the fourth location at the fourth time; and
    aggregating logs of locations and conditions of the first needle into a first path of the first needle during the surgery.

2. The method of claim 1:
    further comprising, in response to detecting the needle package in the first image:
        detecting an identifier of the needle package in the first image;
        retrieving a count of needles, contained in the needle package, associated with the identifier; and
        incrementing a sterile packaged needle counter by the count of needles;
    wherein logging the first needle in the sterile packaged condition at the first location at the first time comprises logging the count of needles, comprising the first needle, in the sterile packaged condition at the first location at the first time in response to detecting the needle package in the first image;
    further comprising, in response to detecting features representative of the first needle in the second region of the second image:
        incrementing a deployed needle counter for the first needle; and
        decrementing the sterile packaged needle counter for the first needle;
    further comprising, in response to detecting features representative of the needle disposal container in the fourth region of the fourth image:
        incrementing a returned used needle counter for the first needle; and
        decrementing the deployed needle counter for the first needle.

3. The method of claim 2, further comprising, in response to the deployed needle counter exceeding the returned used needle counter by more than a threshold quantity of needles for more than a threshold duration of time:
    issuing an alarm for manual survey of needles in the surgical space; and
    serving a prompt, to surgical staff in the surgical space, to return a quantity of loose needles, equal to the deployed needle counter, to the needle disposal container.

4. The method of claim 2, further comprising:
    in response to detecting the needle package in the first image, logging a second needle in the sterile packaged condition at the first location at the first time according to the count of needles;
    in response to detecting a second needle driver at a fifth location in a fifth image, in the sequence of images, captured at a fifth time succeeding the first time:

scanning a fifth region of the fifth image depicting a distal end of the second needle driver for features representative of the second needle; and
in response to detecting features representative of the second needle in the fifth region of the fifth image:
  logging the second needle in the sterile retained condition proximal the fifth location at the fifth time;
  incrementing the deployed needle counter for the second needle; and
  decrementing the sterile packaged needle counter for the second needle; and
in response to the sterile packaged needle counter falling below a threshold quantity of needles, serving a prompt, to surgical staff in the surgical space, to enter a second needle package into the surgical space.

5. The method of claim 1, further comprising:
in response to detecting the needle package in the first image, logging a second needle in the sterile packaged condition at the first location at the first time according to the count of needles;
in response to detecting a second needle driver at a fifth location in a fifth image, in the sequence of images, captured at a fifth time succeeding the first time:
  scanning a fifth region of the fifth image depicting a distal end of the second needle driver for features representative of the second needle; and
  in response to detecting features representative of the second needle in the fifth region of the fifth image, logging the second needle in the sterile retained condition proximal the fifth location at the fifth time;
tracking the second needle driver in a subsequence of images, succeeding the fifth image, in the sequence of images;
verifying presence of features representative of the second needle proximal the distal end of the second needle driver in the subsequence of images; and
in response to detecting absence of features representative of the second needle proximal the distal end of the second needle driver in a sixth image succeeding the fifth image:
  detecting loss of the second needle from the second needle driver at a sixth time;
  activating an alarm for loss of the second needle;
  calculating a probability map of locations of the second needle at the sixth time based on a location of the second needle in the surgical space at the sixth time; and
  presenting the probability map to surgical staff in the surgical space.

6. The method of claim 1:
wherein accessing the sequence of images comprises:
  accessing a first subsequence of images, comprising the first image and the second image, from a first cluster of optical sensors, in the set of optical sensors, facing and configured to image an inventory field at a first optical resolution, the first location and the second location located within the inventory field; and
  accessing a second subsequence of images, comprising the third image, from a second cluster of optical sensors, in the set of optical sensors, facing and configured to image an operating field at a second optical resolution, the patient located within the operating field; and
further comprising:
  accessing a third subsequence of images, in the sequence of images, from a third cluster of optical sensors, in the set of optical sensors, facing and configured to image an intermediate field between the inventory field and the operating field at a third optical resolution less than the first optical resolution and the second optical resolution;
  tracking needles, removed from the needle package, in the inventory field based on locations of features representative of needles detected in the first subsequence of images;
  tracking needles, manipulated near the patient, in the operating field based on locations of features representative of needles detected near distal ends of needle drivers detected in the second subsequence of images; and
  tracking needles moving between the inventory field and the operating field based on locations of features representative of needle drivers detected in the third subsequence of images.

7. The method of claim 1, further comprising:
in response to detecting the needle package in the first image, logging a second needle in the sterile packaged condition at the first location at the first time based on a quantity of sterile needles contained in the needle package;
in response to detecting a second needle driver at a fifth location in a fifth image, in the sequence of images, captured at a fifth time succeeding the first time:
  scanning a fifth region of the fifth image depicting a distal end of the second needle driver for features representative of the second needle; and
  in response to detecting features representative of the second needle in the fifth region of the fifth image, logging the second needle in the sterile retained condition proximal the fifth location at the fifth time;
in response to detecting the second needle driver at a sixth location in a sixth image, in the sequence of images, captured at a sixth time succeeding the fifth time:
  scanning a sixth region of the sixth image depicting the distal end of the second needle driver for features representative of the patient; and
  in response to detecting features representative of the patient in the third region of the third image, logging the first needle in a used retained condition proximal the third location at the third time;
in response to detecting the second needle driver at a seventh location in a seventh image, in the sequence of images, captured at a seventh time succeeding the sixth time:
  scanning a seventh region of the seventh image depicting the distal end of the second needle driver for features representative of the needle disposal container; and
  in response to detecting features representative of the needle disposal container in the seventh region of the seventh image, logging the second needle in the disposed condition proximal the seventh location at the seventh time;
aggregating logs of locations and conditions of the second needle into a second path of the second needle during the surgery;
calculating a variance between the first path of the first needle and the second path of the second needle; and
predicting a scope of post-operative complications for the patient based on the variance.

8. The method of claim 1, further comprising:
tracking the first needle in a subsequence of images succeeding the third image;

detecting proximity of the first needle to the patient in the subsequence of images;
calculating a sequence of retention risks for retention of the first needle in the patient based on proximity of the first needle to the patient integrated over time;
generating an alarm in response to the retention risk exceeding a threshold risk; and
augmenting the first path of the first needle with sequence of retention risks for retention of the first needle in the patient.

9. A method for monitoring needle consumption in a surgical space during a surgery includes:
accessing a sequence of images of a surgical space captured by a set of optical sensors arranged in the surgical space;
in response to detecting a needle package in a first image, in the sequence of images, of an inventory field in the surgical space, logging entry of a first set of needles in a sterile packaged condition at the inventory field at a first time;
for each needle in the first set of needles:
in response to detecting a needle driver in a second image, in the sequence of images, of the inventory field:
scanning the second image for a needle proximal a distal end of the needle driver; and
in response to detecting the needle proximal the distal end of the needle driver in the second image, logging the needle in a sterile retained condition in the inventory field at a second time;
in response to detecting the needle driver in a third image, in the sequence of images, of an operating field in the surgical space:
scanning the third image for features representative of a patient proximal the distal end of the needle driver; and
in response to detecting features representative of the patient proximal the distal end of the needle driver in the third image, logging the needle in a used retained condition proximal the patient at a third time;
aggregating logs of locations and conditions of the needle into a path of the needle during the surgery; and
storing the path of the needle with a set of needle paths occurring during the surgery; and
characterizing performance during the surgery based on the path of the needle and the set of needle paths occurring during the surgery.

10. The method of claim 9, further comprising:
in response to detecting the needle package in the first image, incrementing a sterile packaged needle counter by a count of needles contained in the needle package;
for each needle in the set of needles:
in response to detecting, in the sequence of images, a needle removed from the needle package in the inventory field:
incrementing a deployed needle counter for the needle; and
decrementing the sterile packaged needle counter for the needle;
in response to detecting a needle driver associated with the needle in a fourth image in the sequence of images:
scanning the fourth image for a needle disposal container; and in response to detecting the needle disposal container in the fourth image:
logging the needle in a disposed condition;
incrementing a used contained needle counter for the needle; and
decrementing the deployed needle counter for the needle.

11. The method of claim 9, wherein characterizing performance during the surgery comprises:
calculating a variance between paths of needles in the set of needle paths;
characterizing a complexity of the surgery proportional to the variance; and
predicting a scope of post-operative complications for the patient based on the complexity.

12. The method of claim 9, wherein characterizing performance during the surgery comprises:
accessing a type of the surgery;
accessing a corpus of needle paths recorded during a set of past surgeries of the type of the surgery;
characterizing a difference between the set of needle paths and the corpus of needle paths; and
in response to the difference between the set of needle paths and the corpus of needle paths exceeding a threshold:
prompting the surgical staff to confirm intent of the difference; and
associating a remark, entered by the surgical staff member, with the surgery.

13. The method of claim 12, further comprising:
in response to the difference between the set of needle paths and the corpus of needle paths exceeding a threshold, serving a visualization of the surgery to a surgical staff member associated with the surgery;
in response to the remark, entered by the surgical staff member, confirming intent of the difference between the set of needle paths and the corpus of needle paths, prompting investigation of the set of needle paths for an improved needle handling process; and
in response to the remark, entered by the surgical staff member, contradicting intent of the difference between the set of needle paths and the corpus of needle paths, prompting needle handling training for the surgical staff member.

14. The method of claim 12, wherein accessing the corpus of needle paths recorded during the set of past surgeries of the type comprises:
identifying a surgical staff member present in the surgical space during the surgery; and
accessing the corpus of needle paths recorded during the set of past surgeries, of the type, performed by the surgical staff member.

15. The method of claim 9, wherein characterizing performance during the surgery comprises:
calculating a characteristic of the set of needle paths;
accessing a type of the surgery;
accessing a first characteristic of a first corpus of needle paths recorded during a first set of past surgeries, of the type, associated with a first magnitude of post-operative patient complications;
accessing a second characteristic of a second corpus of needle paths recorded during a second set of past surgeries, of the type, associated with a second magnitude of post-operative patient complications greater than the first magnitude; and predicting a scope of post-operative complications for the patient based on proximity of the characteristic of the set of needle paths to the first characteristic and to the second characteristic.

16. A method for monitoring needle consumption in a surgical space during a surgery includes:
- accessing a sequence of images captured by a set of optical sensors facing an inventory field within the surgical space;
- scanning the sequence of images for features representative of needle packages and needles;
- in response to detecting entry of a needle package into the surgical space in a first image, in the sequence of images:
  - logging entry of the needle package, labeled as sterile, into the inventory field at a first time; and
  - incrementing a sterile packaged needle counter for the needle package according to a first quantity of sterile needles associated with a type of the needle package;
- in response to detecting removal of a first needle from the inventory field in a second image, in the sequence of images:
  - incrementing a deployed needle counter at a second time succeeding the first time; and
  - decrementing the sterile packaged needle counter; and
- in response to detecting return of the first needle to the inventory field in a third image, in the sequence of images:
  - labeling the first needle in the third image as used at a third time succeeding the second time; and
  - decrementing the deployed needle counter.

17. The method of claim 16, further comprising:
- in response to detecting return of the first needle to the inventory field in the third image:
  - labeling the first needle as uncontained at the third time; and
  - tracking the first needle in a subsequence of images succeeding the third image; and
- in response to detecting insertion of the first needle into the needle package in a fourth image, in the sequence of images, succeeding the subsequence of images:
  - associating the first needle with the needle package;
  - relabeling the needle package as unsterile;
  - incrementing a contained used needle counter for the first needle and by a value of the sterile packaged needle counter at the fourth time; and
  - clearing the sterile packaged needle counter for the needle package.

18. The method of claim 16, further comprising:
- in response to detecting return of the first needle to the inventory field in the third image:
  - incrementing an uncontained used needle counter at the third time; and
  - tracking the first needle in a subsequence of images succeeding the third image; and
- in response to detecting insertion of the first needle into a sharps container in a fourth image, in the sequence of images, succeeding the subsequence of images:
  - associating the first needle with the sharps container;
  - incrementing a contained used needle counter; and
  - ceasing tracking of the first needle.

19. The method of claim 16, further comprising:
scanning a first subsequence of images, in the sequence of images, succeeding the first image, for a needle driver;
- in response to detecting the needle driver in a fourth image, in the first subsequence of images:
  - detecting a distal end of the needle driver in a subregion of the fourth image;
  - scanning the subregion of the fourth image for the needle package; and
  - in response to detecting the needle package in the subregion of the fourth image, activating a driver approach flag;
- in response to detecting the needle package within a threshold distance of the distal end of the needle driver in a fifth image, succeeding the fourth image in the first subsequence of images, while the driver approach flag is active:
  - activating a needle removal flag;
- in response to detecting withdrawal of the needle driver from the needle package in a sixth image, succeeding the fifth image in the first subsequence of images, while the needle removal flag is active:
  - detecting the distal end of the needle driver in a subregion of the sixth image;
  - scanning the subregion of the sixth image for the first needle; and
  - in response to detecting the first needle in the subregion of the sixth image, detecting removal of the first needle from the needle driver;
- tracking the needle driver in a second subsequence of images, in the sequence of images, succeeding the sixth image; and
- in response to detecting the distal end of the needle driver outside a boundary of the inventory field in the second image, detecting removal of the first needle from the inventory field.

20. The method of claim 16, further comprising:
- in response to detecting return of the first needle to the inventory field in the third image, incrementing a returned used needle counter; and
- in response to the deployed needle counter a threshold quantity of needles for more than a threshold duration of time:
  - issuing an alarm for manual survey of needles in the surgical space; and
  - serving a prompt, to surgical staff in the surgical space, to return a quantity of loose needles, equal to a difference between the deployed needle counter and the threshold quantity of needles, to the needle disposal container.

* * * * *